US005672472A

United States Patent [19]
Ecker et al.

[11] Patent Number: 5,672,472
[45] Date of Patent: Sep. 30, 1997

[54] SYNTHETIC UNRANDOMIZATION OF OLIGOMER FRAGMENTS

[75] Inventors: David J. Ecker, Leucadia; Jacqueline Wyatt, Carlsbad; Thomas W. Bruice, Carlsbad; Kevin Anderson, Carlsbad; Ronnie C. Hanecak, San Clemente; Timothy Vickers, Oceanside; Peter Davis, Carlsbad, all of Calif.

[73] Assignee: ISIS Pharmaceuticals, Inc., Carlsbad, Calif.

[21] Appl. No.: 196,103

[22] PCT Filed: Aug. 21, 1992

[86] PCT No.: PCT/US92/07121

§ 371 Date: Feb. 22, 1994

§ 102(e) Date: Feb. 22, 1994

[87] PCT Pub. No.: WO93/04204

PCT Pub. Date: Mar. 4, 1993

Related U.S. Application Data

[63] Continuation-in-part of Ser. No. 749,000, Aug. 23, 1991, abandoned.

[51] Int. Cl.[6] ............................ C12Q 1/70; C12Q 1/68; C07H 21/00; C12P 19/34
[52] U.S. Cl. ............................ 435/6; 435/5; 435/91.1; 536/25.3
[58] Field of Search ............................ 435/5, 6, 91.1; 536/25.3

[56] References Cited

U.S. PATENT DOCUMENTS

| | | | |
|---|---|---|---|
| 4,833,092 | 5/1989 | Geysen | 436/501 |
| 5,010,175 | 4/1991 | Rutter et al. | 530/334 |
| 5,194,392 | 3/1993 | Geysen | 436/518 |

FOREIGN PATENT DOCUMENTS

| | | |
|---|---|---|
| 8403564 | 9/1984 | WIPO. |
| 8600991 | 2/1986 | WIPO. |
| 8701374 | 3/1987 | WIPO. |
| 9112331 | 8/1991 | WIPO. |
| 9200091 | 1/1992 | WIPO. |
| 9205285 | 4/1992 | WIPO. |
| WO 92/09300 | 6/1992 | WIPO. |

OTHER PUBLICATIONS

Fodor et al., Light–Directed, Spatially Addressable Parallel Chemical Synthesis *Science* 1991 251:767–773.
Riordan et al. (1991 Apr) "Oligonucleotide–Based Therapeutics" *Nature* 350: 442–443.
Sullenger et al. (1990) "Overexpression of TAR Sequences Renders Cells Resistant to Human Immunodeficiency Virus Replication" *Cell* 63:601–608.
Vickers et al., "Inhibition of HIV–LTR Gene Expression By Oligonucleotides Targeted to the TAR Element" *Nuc. Acids. Res.* 19: 3359–3368 (1991).
Mason et al., "Diversity of the Antibody Response" *Vaccines* 86: 97–103 (1986).
Geysen et al., "Strategies for Epitope Analysis Using Peptide Synthesis", *J. Immunol Meth.* 102: 259–274 (1987).
Van Der Zee et al., "Efficient Mapping and Characterization of a T Cell Epitope by the Simultaneous Synthesis of Multiple Peptides", Characterization *Eur. J. Immunol* 19: 43–47 (1989).
Vickers et al., Abstract only *Nucleic Acids. Res.* 19: 3359–3368 (1991).
Houghten et al., "Generation and Use of Synthetic Peptide Combinatorial Libraries for Basic Research and Drug Discovery", *Nature* 354: 84–86 (1991).
Tuerk and Gold, "Systematic Evolution of Ligands by Exponential Enrichment: RNA Ligands to Bacteriophage T4 DNA Polymerase", *Science* 249: 505–510 (1990).
Ellington and Szostak, "In Vitro Selection of RNA Molecules That Bind Specific Ligands", *Nature* 346: 818–822 (1990).
Yamada, "Adhesive Recognition Sequences", *J. Biol. Chem.* 266: 12809–12812 (1991).
Dustin and Springer, "Lymphocyte Function–Associated Antigen–1 (LFA–1) Interaction Adhesion Molecule–1 (ICAM–1) is One of At Least Three Mechanisms for Lymphocyte Adhesion to Cultured Endothelial Cells", *J. Cell. Biol.* 107: 321–331 (1988).
Bock et al., "Selection of Single–Stranded DNA Molecules That Bind and Inhibit Human Thrombin" *Nature* 355: 564–566 (1992).
Green et al., "In Vitro Genetic Analysis of the Tetrahymena Self–Splicing Intron", *Nature* 347: 406–408 (1990).
Robertson and Joyce, "Selection In Vitro of an RNA Enzyme that Specifically Cleaves Single–Stranded DNA", *Nature* 344: 467–468 (1990).
Joyce, "Amplification, Mutation and Selection of Catalytic RNA", *Gene* 82: 83–87 (1989).

(List continued on next page.)

*Primary Examiner*—Jasemine C. Chambers
*Assistant Examiner*—Scott D. Priebe
*Attorney, Agent, or Firm*—Woodcock Washburn Kurtz Mackiewicz & Norris LLP

[57] ABSTRACT

Methods useful for the determination of oligomers which have specific activity for a target molecule from a pool of primarily randomly assembled subunits are provided. The disclosed methods involve repeated syntheses of increasingly simplified sets of oligomers coupled with selection procedures for determining oligomers having the highest activity. Freedom from the use of enzymes allows the application of these methods to any molecules which can be oligomerized in a controlled fashion.

64 Claims, 7 Drawing Sheets

OTHER PUBLICATIONS

Chittenden et al., "The T/E1A–Binding Domain of the Retinoblastoma Product Can Interact Selectively With a Sequence–Specific DNA–Binding Protein", *Cell* 65: 1073–1082 (1991).

Kinzler and Vogelstein, "The GLI Gene Encodes a Nuclear Protein Which Binds Specific Sequences in the Human Genome", *Molec. Cell. Biol.* 10: 634–642 (1990).

Thiesen and Bach, "Target Detection Assay (TDA) : A Versatile Procedure to Determine DNA Binding Sites as Demonstrated On SP1 Protein", *Nucleic Acid Research* 18: 3203–3209 (1990).

Kinzler and Vogelstein, "Whole Genome PCR: Application to the Indentification of Sequences Bound by Gene Regulatory Proteins", *Nucleic Acid Research* 17: 3645–3653 (1989).

Blackwell and Weintraub, "Differences and Similarities in DNA–Binding Preferences of MyoD and E2A Protein Complexes Revealed by Binding Site Selection", *Science* 250: 1104–1110 (1990).

Blackwell et al, "Sequence–Specific DNA Binding by the c–Myc Protein", *Science* 250: 1149–1151 (1990).

Geysen et al, "A Priori Delineation of a Peptide Which Mimics a Discontinuous Antigenic Determinant", *Molecular Immunology* 23: 709–715 (1986).

Ecker et al., "Rational Screening of Oligonucleotide Combinatorial Libraries for Drug Discovery", *Nuc. Acids Res* 21: 1853–1856 (1993).

Wyatt et al., "Combinatorially Selected Guanosine–Quartet Structure is a Potent Inhibitor of Human Immunodeficiency Virus Envelope–Mediated Cell Fusion".

```
    G G
  U   G
  C    A
   C·G
   G·C
   A·U
 U G·C
C  A·U
 U G·C
   A·U
   C·G
   C·G
   G·C
SEQ ID NO: 20
```

```
   C-A
  A   A
  U   G
   C:G
   C:G
   U:A
   U:A
   C:G
   C:G
   G:C
   G:C
   U:A
   C:G
```

SYNTHETIC UNRANDOMIZATION OF OLIGOMER FRAGMENTS

CROSS REFERENCE TO RELATED APPLICATIONS

This application is a continuation-in-part of U.S. Ser. No. 749,000 filed Aug. 23, 1991, now abandoned entitled "Synthetic Unrandomization of Oligomer Fragments" and assigned to the assignee of the present application. The entire disclosure of this application is incorporated by reference herein.

FIELD OF THE INVENTION

This invention relates to the development of drugs and of biologically active diagnostics and research reagents. In particular, this invention relates to the synthetic unrandomization of oligomer fragments to determine fragments specifically active for target molecules.

BACKGROUND OF THE INVENTION

Oligomers may be designed which are useful for therapeutic, diagnostic and research applications. In the past, development of biologically active oligomer substances was often limited to the modification of known sequences, unit by unit, until a desired Characteristic or efficacy was achieved. However, in addition to time drawbacks, protocols employing these types of methodologies are limiting in that the final product is based upon, and often not far removed from, the structure of the starting material.

Recently, new methods have been developed whereby drugs and biologically active substances can be "designed." A variety of combinatorial strategies have been described to identify active peptides. Houghton, et al. *Nature* 1991, 354, 84; Lam, et al., *Nature* 1991, 354, 82; Owens, et al., *Biochem. Biophys. Res. Commun.* 1991, 181, 402; Fodor, et al., *Science* 1991, 251, 767; Geysen, et al., *Molecular Immunology* 1986, 23, 709; Zuckermann, et al., *Proc. Natl. Acad. Sci.* 1992, 89, 4505; Rutter, et al., U.S. Pat. No. 5,010,175 issued Apr. 23, 1991.

Focusing on the field of nucleic acid-protein binding, combinatorial nucleic acid selection methods generally select for a specific nucleic acid sequence from a pool of random nucleic acid sequences based on the ability of selected sequences to bind to a target protein. The selected sequences are then commonly amplified and the selection process repeated until a few strong binding sequences are identified. These methods generally employ enzymatic steps within the protocol. Commonly T7 RNA polymerase and Taq I associated with polymerase chain reaction amplification methods are employed. One group recently identified a target sequence to the RNA-binding protein gp43. Tuerk and Gold, *Science* 1990 249, 505. Tuerk and Gold's "systematic evolution of ligands by exponential enrichment" (SELEX) method identified specifically bindable RNA sequences using four cycles of amplification of RNA sequences having variable portions therein and which were specifically bindable to gp43.

Another group designed DNA molecules which recognized the protease thrombin. Bock, et al., *Nature* 1992, 355, 564. This method involves the preparation of a population involving a random region flanked by known primer regions followed by PCR amplification and selection. Small molecule mimics of metabolic cofactors have been selectively recognized by RNA sequences in this manner by Ellington and Szostak, *Nature* 1990, 346, 818. These techniques were suggested to be useful to design oligonucleotide ligands, however their dependence upon enzymatic means for amplification and sequence determination limits their uses. Simpler methods for the identification of useful oligomers which are specifically bindable to target molecules and which express specific activity for target molecules are greatly desired. Methods which are not dependent upon enzymatic means would simplify protocols as well as expand the range of substrates with which the protocols would be effective. For example, presently there are over one hundred nucleotide analogs available. Cook, P. D., *Anti-Cancer Drug Design* 1991, 6, 585 and Uhlmann, et al., *Chem. Rev.* 1990, 90, 544. Since not all analogs are amenable to enzymatic processes, a non-enzymatic means for determining useful oligomer sequences which are specifically bindable to target sequences is greatly desired. Such methods could determine oligomers which are specifically bindable, not only to natural RNA-binding proteins, but also to any protein, nucleic acid, or other target molecule.

Methods are also greatly desired for determining useful oligomer sequences having particular desired activity, not limited to binding of target molecules. Such activity may include, but is not limited to, enzymatic or catalytic activity.

BRIEF DESCRIPTION OF THE DRAWINGS

FIG. 1 is a schematic representation of the nucleotide sequence and Secondary structure of the ras 47-base-pair stem/loop RNA (SEQ ID NO:1).

SUMMARY OF THE INVENTION

Figure 2A:
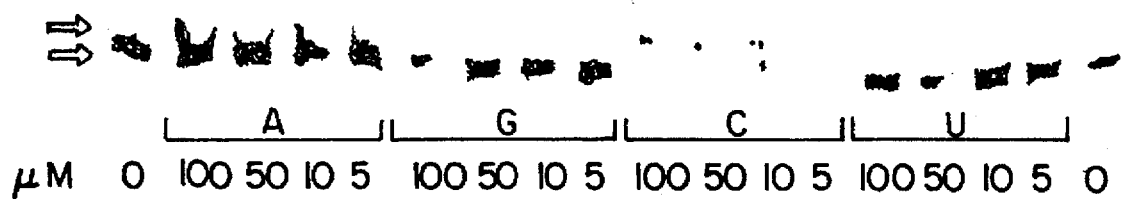
FIG. 2A–2C representations of a gel image of a gel shift assay showing binding affinity of RNA oligonucleotides with ras 47-base-pair stem/loop RNA.

Combinatorial strategies offer the potential to generate and screen extremely large numbers of compounds and to identify individual molecules with a desired binding specificity or pharmacological activity. This invention is directed to substantially non-enzymatic methods of determining oligomers which are specifically active for target molecules. Such oligomers preferably exhibit desired activity such as enzymatic or catalytic activity as well as binding affinity.

Methods of the present invention are useful for the determination of oligomers which have specific activity for target molecule from a pool of primarily randomly assembled subunits. Said methods involve repeated syntheses of increasingly simplified sets of oligomers coupled with selection procedures for determining the oligomer set having the greatest activity in an assay for desired activity.

Simplification of the pool occurs because, with each additional step of the methods, at least one additional position in the oligomer is determined. As a result, the possible number of different oligomer molecules in the pool decreases sequentially with the number of random positions remaining in the oligomer.

Freedom from the use of enzymes allows the application of these methods to any molecules which can be oligomerized in a controlled fashion.

In one embodiment of the present invention, methods for making oligonucleotides having specific activity for a target molecule are provided. These methods involve preparing a group comprising a plurality of sets of oligonucleotides, each oligonucleotide comprising at least four base units, by defining a common position in the oligonucleotides of the sets and synthesizing said sets of oligonucleotides such that each set has a different base unit in said common position and the base units which are not in the common position are randomized. Each of the sets are then assayed for activity against the target molecule and the set having the greatest activity for the target molecule is selected.

In other embodiments of the present invention each group of oligonucleotides may be subfractionated to provide subfractions of the sets of oligonucleotides. Each subfraction may be assayed against the target molecule and the set from which the subfraction having the highest activity was derived is selected.

These methods further comprise preparing a further group comprising a plurality of sets of oligonucleotides, each of the sets having in the previously defined common position the base unit appearing in the previously defined common position in the previously selected set. Each of said further group of sets has a different base unit in an additional, defined common position. The base units in positions of the oligonucleotides which are not in a common position are randomized. In other embodiments of the invention this group may subfractionated to provide subfractions of the sets of oligonucleotides.

Each of said sets or subfractions of sets may be assayed for activity for the target molecule and the set having the highest activity, or the set from which the subfraction having the highest activity was derived, is selected. The preceding steps may be performed iteratively.

Methods of determining an oligonucleotide cassette having specific activity for a target molecule are also provided by the present invention. These methods involve preparing a group comprising a plurality of sets of oligonucleotides, each oligonucleotide comprising at least four base units, by defining a common position in the oligonucleotides of the sets and synthesizing said sets of oligonucleotides such that each set has a different base unit in said common position and the base units which are not in the common position are randomized. Each of the sets are then assayed for activity for a target molecule and the set having the greatest activity for the target molecule is selected. Thereafter, a further group is prepared comprising a plurality of sets of oligonucleotides, each of the sets having in the previously defined common position the base unit appearing in the previously defined common position in the previously selected set. Each of said further group of sets has a different base unit in an additional defined common position. The base units in positions of the oligonucleotides which are not in a defined common position are randomized. Each set of said further group is assayed for specific activity for the target molecule and the set having the highest activity is selected. The preceding steps are performed iteratively to provide an oligonucleotide cassette having each position defined.

In other embodiments of the invention, methods for determining an oligonucleotide having specific activity for a target molecule are provided. Such methods comprise preparing a group comprising a plurality of sets of oligonucleotides, each of the oligonucleotides comprises at least one oligonucleotide cassette and at least one flanking region. A common position is defined in a flanking region of the oligonucleotides of the sets and the sets of oligonucleotides are synthesized such that each set has a different base unit in said common position and the base units which are not in the common position are randomized. Each of the sets are then assayed for activity for a target molecule and the set having the greatest activity for the target molecule is selected.

These methods also may comprise preparing a further group comprising a plurality of sets of oligonucleotides, each of the sets having in the previously defined common position the base unit appearing in the previously defined common position in the previously selected set. Each of said further group of sets having a different base unit in an additional, defined common position in the flanking region. The base units in positions of the oligonucleotides which are not in a common position in the flanking region are randomized. Each of the sets of oligonucleotides are assayed for specific activity for the target molecule and the set having the highest activity is selected. The preceding steps may be and preferably are performed iteratively.

In another embodiment of the present invention, methods for making polypeptides having specific activity for a target molecule are provided. These methods involve preparing a group comprising a plurality of sets of polypeptides, each polypeptide comprising at least four amino acids units by defining a common position in the polypeptides of the sets and synthesizing said sets of polypeptides such that each set has a different amino acid unit in said common position, the amino acid units which are not in said common position being randomized. Each of the sets is then assayed for activity and the set having the most activity is selected.

In yet another embodiment of the present invention each group of polypeptides is subfractionated to provide subfractions of the sets of polypeptides. Each subfraction may be assayed against the target molecule and the set from which the subfraction having the highest activity was derived is selected.

These methods further may comprise preparing a further group comprising a plurality of sets of polypeptides, each of the sets having in the previously defined common position the amino acid unit appearing in the previously defined common position in the previously selected set. Each of said further group of sets has a different amino acid unit in an additional, defined common position. The amino acid units in positions of the polypeptide which are not in a common position are randomized. In other embodiments of the invention this group may subfractionated to provide subfractions of the sets of polypeptides.

Each of said sets or subfractions of sets may be assayed for activity for the target molecule and the set having the highest activity, or the set from which the subfraction having the highest activity was derived, is selected. The preceding steps may be performed iteratively.

Methods of determining a polypeptide cassette having specific activity for a target molecule are also provided by the present invention. These methods involve preparing a group comprising a plurality of sets of polypeptides, each polypeptide comprising at least four amino acid units, by defining a common position in the polypeptides of the sets and synthesizing said sets of polypeptides such that each set has a different amino acid unit in said common position and the amino acid units which are not in the common position are randomized. Each of the sets are then assayed for activity for a target molecule and the set having the greatest activity for the target molecule is selected. Thereafter, a further group is prepared comprising a plurality of sets of polypeptides, each of the sets having in the previously defined common position the amino acid unit appearing in the previously defined common position in the previously selected set. Each of said further group of sets has a different amino acid unit in an additional defined common position. The amino acid units in positions of the polypeptides which are not in a defined common position are randomized. Each set of said further group is assayed for specific activity for the target molecule and the set having the highest activity is selected. The preceding steps are performed iteratively to provide a polypeptide cassette having each position defined.

In other embodiments of the invention methods for determining a polypeptide having specific activity for a target molecule are provided comprising preparing a group comprising a plurality of sets of polypeptides, each polypeptide comprising at least one polypeptide cassette and at least one flanking region by defining a common position in a flanking region of the polypeptides of the sets and synthesizing said sets of polypeptides such that each set has a different amino acid unit in said common position and the amino acid units which are not in the common position are randomized. Each of the sets are then assayed for activity for a target molecule and the set having the greatest activity for the target molecule is selected.

These methods further comprise preparing a further group comprising a plurality of sets of polypeptides, each of the sets having in the previously defined common position the amino acid unit appearing in the previously defined common position in the previously selected set. Each of said further group of sets has a different amino acid unit in an additional, defined common position in the flanking region. The amino acid units in positions of the polypeptides which are not in a common position in the flanking region are randomized. Each of the sets of polypeptides are assayed for specific activity for the target molecule and the set having the highest activity is selected. The preceding steps may be performed iteratively.

DETAILED DESCRIPTION OF THE INVENTION

The present invention is directed to non-enzymatic methods for determining oligomers which are active for a target molecule. In one embodiment of the present invention methods of determining oligonucleotides having specific binding affinity for a target molecule are provided. Another embodiment of the present invention provides methods determining oligonucleotides having enzymatic or catalytic activity for a target molecule. In still other embodiments of the present invention methods of determining polypeptides having specific binding affinity for a target molecule are provided. Methods of determining polypeptides having enzymatic or catalytic activity for a target molecule are also provided.

In the context of the present invention an oligomer is a string of units linked together by chemically similar covalent linkages. Nucleic acids linked together via phosphodiester bonds or amino acids linked together via peptide bonds are examples of naturally occurring oligomers.

In the context of this invention, the term "oligonucleotide" refers to a polynucleotide formed from naturally occuring bases and furanosyl groups joined by native phosphodiester bonds. This term effectively refers to naturally occurring species or synthetic species formed from naturally occurring subunits or their close homologs. The term "oligonucleotide" may also refer to moieties which have portions similar to naturally occurring oligonucleotides but which have non-naturally occurring portions. Thus, oligonucleotides may have altered sugar moieties or inter-sugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the stability of the oligonucleotide or the ability of the oligonucleotide to penetrate into the region of cells where the viral RNA is located. It is preferred that such substitutions comprise phosphorothioate bonds, phosphotriesters, methyl phosphonate bonds, short chain alkyl or cycloalkyl structures or short chain heteroatomic or heterocyclic structures. Most preferred are $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ structures where phosphodiester is O—P—O—$CH_2$). Also preferred are morpholino structures. Summerton, J. E. and Weller, D. D., U.S. Pat. No. 5,034,506 issued Jul. 23, 1991. In other preferred embodiments, such as the protein-nucleic acid (PNA) backbone, the phosphodiester backbone of the oligonucleotide may be replace with a polyamide backbone, the bases being bound directly or indirectly to the aza nitrogen atoms of the polyamide backbone. P. E. Nielsen, et al., *Science* 1991 254 1497. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Similarly, modifications on the furanosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nN_2$, $O(C_2)_nCH_3$ where n is from 1 to about 10; $C_1$ to $C_{10}$ lower alkyl, substituted lower alkyl, alkaryl or aralkyl; Cl, Br, CN, C₃, OCF₃, O—, S—, or N— alkyl; O—, S—, or N-alkenyl; SOCH₃, SO₂CH₃; ONO₂; N₃; N₃; NH₂; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyls may also be used in place of the pentofuranosyl group. Oligonucleotides may also comprise other modifications consistent with the spirit of this invention. Such oligonucleotides are best described as being functionally interchangeable with yet structurally distinct from natural oligonucleotides. All such oligonucleotides are comprehended by this invention so long as they effectively function as subunits in the oligonucleotide.

In the context of the present invention polypeptide refers to a plurality of joined amino acid units formed in a specific sequence from naturally occurring amino acids. Said amino acid units are generally linked together via peptide bonds. Naturally occurring subunits include the twenty commonly occurring amino acids, as well as other less common naturally occurring amino acids. Polypeptides, in the context of the present invention, also refers to moieties which are similar to polypeptides but which have non-naturally occurring portions. Hence, polypeptides may have altered linkages or may be comprised of altered amino acid residues such as D-amino acids or other modifications consistent with the spirit of the present invention. Such modified polypeptides have also been referred to in the art as polypeptide analogs.

The methods of the present invention are useful to determine oligomers which are specifically active for a target molecule. In the context of the present invention determine refers to concurrent identification of the sequence of an oligomer and the binding activity of the oligomer for a target molecule. Further, determine refers to the identification of oligomers having activity such as catalytic or enzymatic activity. In some instances, neither the oligomer sequence nor its specific activity is known prior to performance of methods of the present invention. In other cases, while a particular oligomer sequence may be known, those skilled in the art may not recognize its activity for a particular target molecule. In still other cases, activity of a known sequence for a particular target molecule may be optimized.

Oligomers of the present invention are assayed for specific activity for a target molecule. In some embodiments of the present invention, specific activity refers to binding affinity of said oligomers for a target molecule. In other embodiments of the present invention, specific activity encompasses binding affinity and further encompasses activity such as catalytic or enzymatic activity. As used herein, binding affinity refers to the ability of the oligomer to bind to a target molecule via hydrogen bonds, van der Waals interactions, hydrophobic interactions, or otherwise. For example, an oligonucleotide may have binding affinity for another oligonucleotide to which it is complementary, i.e., to which it has the ability to hybridize due to Watson-Crick base pair attraction.

Target molecules of the present invention may include any of a variety of biologically significant molecules. Target molecules may be nucleic acid strands such as significant regions of DNA or RNA. Target molecules may also be proteins, carbohydrates, or glycoproteins. In some preferred embodiments of the present invention, said target molecule is a protein such as an immunoglobulin, receptor, receptor binding, ligand, antigen or enzyme and more specifically may be a phospholipase, tumor necrosis factor, endotoxin, interleukin, plasminogen activator, protein kinase, cell adhesion molecule, lipoxygenase, hydrolase or transacylase. In other preferred embodiments of the present invention said target molecules may be important regions of the human immunodeficiency virus, Candida, herpes viruses, papillomaviruses, cytomegalovirus, rhinoviruses, hepatitises, or influenza viruses. In still further preferred embodiments of the present invention said target molecule is ras 47-mer stem loop RNA, the TAR element of human immunodeficiency virus or the gag-pol stem loop of human immunodeficiency virus (HIV) or the HIV tat protein. Still other targets may induce cellular activity. For example, a target may induce interferon.

In some aspects of the present invention, a target protein may be identified based upon the fact that proteins bind to free aldehyde groups while nucleic acids do not. Thus, a sampling of proteins which have been identified as potential targets may be bound to solid supports having free aldehyde groups such as nitrocellulose filters. For example, up to 96 proteins may be bound in individual wells of a 96-well nitrocellulose filter manifold. In some embodiments of the present invention sequential concentrations of protein may be tested to determine the effect of lowering the protein target concentration. Thereafter, an identical detectably labeled oligonucleotide group may be incubated with each protein sample under binding conditions. The preparation of labeled oligonucleotide groups is described herein. The support is washed and the presence or absence of binding is detected whereby binding indicates that the oligonucleotide group has specific activity for a given protein. As will be apparent to one skilled in the art, methods of detection of binding will be dependent upon the label used.

In the present invention, a group of sets of random oligomers is prepared. Oligomers may be prepared by procedures known to those skilled in the art. Specifically, oligonucleotides and polypeptides may be prepared by solid state synthesis or by other means known to those skilled in the art. For example, oligonucleotides may be prepared using standard phosphoramidite chemistry. In some embodiments of the present invention oligomer groups may further be labeled, such as by radiolabeling or fluorescent labeling. For example, an oligonucleotide group may be labeled at the 5' termini of the oligonucleotides using [γ-³²P] ATP and T4 polynucleotide kinase. Labeled oligomer groups may be useful in a number of assays which can not be performed using unlabeled oligomer groups.

Oligomers of each set may be of predetermined length. It is preferred that such oligomers be from about 4 to about 50 units in length. It is more preferred that such oligomers be from 4 to about 40 units in length. It is also preferred for some embodiments of the present invention that less than about 10 units of an oligomer are randomized. In some cases, it may be desirable to provide an oligomer which initially comprises 6, 7, or 8 random units.

In some embodiments of the present invention, the length of said oligomer need not be constant throughout the procedure. For example, an 8-mer may be assayed to determined the sequence having highest binding affinity for a target molecule. Subsequently, the 8-mer may be extended and tested as a 15-mer to determine the 15-mer sequence having the highest binding affinity for the target molecule.

Groups of the present invention are made up of a plurality of sets which may remain constant throughout the procedure. From about three to about twenty sets can make up each group. In one preferred embodiment of the present invention four sets make up each group. In another embodiment of the present invention twenty sets make up each group. Alternatively, three sets may make up each group.

The number of sets that make up each group is dependent upon the number of possible distinct chemically similar units which exist for any one species of molecule. For example, an oligonucleotide group may be comprised of four sets since there are four similar units making up the nucleic acid species, i.e. guanine, adenine, cytosine, thymine or adenine, guanine, cytosine and uracil. Alternatively, an oligonucleotide group may be comprised of more than four sets representing for example, the four commonly occurring bases and additional modified bases. Twenty sets may make up a polypeptide group, representing the twenty commonly occurring amino acids, lysine, arginine, histidine, aspartic acid, glutamic acid, glycine, asparagine, glutamine, cysteine, serine, threonine, tyrosine, alanine, valine, leucine, isoleucine, proline, phenylalanine, methionine and tryptophan. Greater than twenty sets may also make up a polypeptide group if uncommon or modified amino acids are included in the assay. Subgroups of basic units may also determine the number of sets in any one group. For example, in procedures to determine a particular polypeptide, sets may represent acidic, basic and neutral amino acid units, i.e. three sets. The number of sets in groups in any one procedure need not remain constant throughout, but may fluctuate. For example, in a one group there may be three sets representing three types of polypeptides and in a next group there may be twenty sets representing each commonly occurring amino acid.

The use of additional units such as nucleotide or amino acid analogs may be preferred in some instances where it is desirable to increase the complexity of the group of oligomers. The complexity of a group may be calculated by the formula $P \times P^N$ where P is the number of different units used and N is the number of positions in an oligomer which are randomized. The complexity of a set (Q) is represented by the formula $P^N$. Table 1 illustrates the change in group complexity as a result of the increase in the number of analogs used. Of course, the number of different units used also determines the number of sets prepared.

TABLE 1

Group Structure = NNN × NNN

| Number of different analogs used (P) | Complexity of each set (Q) ($P^6$) | Total Group Complexity ($P \cdot P^6$) |
| --- | --- | --- |
| 4 | $4^6 = 4096$ | 4 × 4096 = 16,384 |
| 5 | $5^6 = 15,625$ | 5 × 15,625 = 78,125 |
| 6 | $6^6 = 46,656$ | 6 × 46,656 = 279,936 |
| 7 | $7^6 = 117,649$ | 7 × 117,649 = 823,543 |
| 8 | $8^6 = 262,144$ | 8 × 262,144 = 2,097,152 |
| 9 | $9^6 = 531,441$ | 9 × 531,441 = 4,782,969 |
| 10 | $10^6 = 1,000,000$ | 10 × 1,000,000 = 10,000,000 |

Each of the sets in a group has a different unit in a common position of said oligomer. For example, in determining an oligonucleotide, only one of four sets will contain an adenine in a common position, only one set will contain a guanine in a common position, etc. The remaining positions in each set of oligonucleotides are comprised of any combination of random basic units.

In further embodiments of the present invention, common positions are comprised of multiple oligomer positions. For example, for a 9-mer, one common position may be the third position of the 9-mer, or the common position may be comprised of the third position and the fourth position of the 9-mer.

In some aspects of the invention, it may be desirable to begin a procedure by unrandomizing central regions of an oligomer as opposed to end regions, such as the 3' or 5' regions of an oligonucleotide or the carboxy or amino terminal regions of a polypeptide, since it has been found that in some cases defining a central position had a greater affect on specific activity of an oligomer than did defining an end region during a similar stage of a determination. For example, in Example 8 an attempt to fix a 3' position did not yield results that distinguished the sets, whereas a position in the center of the oligomer was fixed to yield results which were detectable.

Furthermore, there is a complexity limit to the detectability of activity (signal-to-noise), especially in oligomers having a high percentage of unrandomized positions. It is likely that with largely unstructured, conformationally dynamic oligomers, a plethora of relatively weak specific activity towards many target molecules will result. As discussed, this may be improved by increasing the number of units used. An additional method of increasing specific activity of a group of oligomers is to constrain the oligomer sterically. For example, an oligonucleotide may be sterically constrained by providing complementary ends at the 3' and 5' termini of the region of interest, which region comprises randomized positions. The complementary ends will hybridize to form a secondary structure.

The detectable specific activity may also be enhanced by the determination and/or use of an oligomer "cassette". An oligomer cassette is a oligomer for which a sequence has been determined. The cassette may be comprised of a sequence of known significance, or may be determined such as by the procedures of the present invention. As used herein an oligonucleotide cassette is a defined oligonucleotide sequence and a polypeptide cassette is a defined polypeptide sequence. In some embodiments of the present invention an oligomer may comprise at least one oligomer cassette and at least one flanking region of unrandomized positions. In other embodiments of the present invention an oligomer may be comprised of more than one cassette wherein each cassette is flanked by at least one region of randomized positions. For example, a oligonucleotide cassette of known sequence may be flanked at the 3' terminus, the 5' terminus, or both the 3' and 5' termini.

In some embodiments of the present invention it may also be desirable to subfractionate a group of oligomers to provide subfractions of the sets of oligomers, thus delimiting the degree of complexity that is assayed at one time. This both diminishes the amount of total material that must be used in a determination in order to have sufficient representation of all individual sequences and it also enhances the signal to noise ratio of the assay by starting with oligomer sets enriched in the most active sequences. Any physical-chemical or functional characteristic, combined with an appropriate separation modality may be used to empirically subfractionate a group, thereby resulting in (or deriving) numerous distinct subfractions of diverse character, and diminished complexity. It is theorized that if a particular fit sequence or sequences exist within the original group for a particular target, it will be found enriched in a limited number of the reduced complexity subfractions.

One skilled in the art would be apprised of the broad selection of appropriate selection modalities which are available. The strategy followed will of course depend upon the properties of the elements of the oligomer group. It will further be appreciated by one skilled in the art that as the number of group elements increases and the structural and chemical diversity enlarges, there will be a greater selection of separation strategies leading to increased subfractionation capacity. By way of example, it is envisioned that novel oligomers may be resolved into subfractions by any one or a combination of size, positive or negative charge, hydrophobicity and affinity interactions. Many chromatographic and analytical instrumental methods are known to those skilled in the art which may be effectively applied to the separation strategies encompassed herein.

In some embodiments of the invention each set of oligomers is assayed for desired activity. In other embodiments of the present invention, identical empirical assays of subfractions of oligomer sets described above are performed in order to identify those subfractions having the strongest activity as indicated by a strong signal to noise ratio. The set having the highest activity or the set from which the subfraction having the highest activity is derived is selected and further unrandomization may be performed if desired.

Specific activity may be detected by methods known to those skilled in the art. Appropriate assays will be apparent to one skilled in the art and oligomer concentration, target molecule concentration, salt concentration, temperature, buffer and buffer concentration may be altered to optimize a particular system. In some preferred embodiments of the present invention, binding conditions simulate physiological conditions. In other preferred embodiments of the present invention binding occurs in a buffer of from about 80 mM to about 110 mM sodium chloride and from about 10 to about 15 mM magnesium chloride. Oligomers may also generally be assayed for catalytic or enzymatic activity.

Gel shift assays may be used to visualize binding of an oligomer to a target molecule. In accordance with methods of the present invention, radiolabelled target molecule bound to oligomer of the present invention may be run on a gel such as a polyacrylamide gel. Bound target molecule has less mobility than unbound target molecule, and therefore will not migrate as far on the gel. The radioactive label allows visualization of the "shift" in mobility by standard procedures for example, by means of X-ray radiography or by using a phosphorimager (Molecular Dynamics). In other embodiments of the present invention a gel shift assay may be performed wherein an unlabeled target molecule may be bound to radiolabelled oligomer.

Radiolabeled oligomer may also be useful for the streptavidin capture of a biotinylated-target bound to an oligomer. For example, a target may be biotinylated prior to incubation with radioactively labeled random oligomer sets. Each set is thereafter incubated with the target under identical conditions and the target molecule is captured on streptavidin-coated beads. Consequently any oligomer which bound to the target will also be captured. Streptavidin-coated beads are available commercially such as for example, streptavidin-coated manganese particles available from Promega. The beads are washed and the reaction may be reequilibrated to further enrich the "winning" sequence. The percent of oligomers from each set which bound is determined by the amount of radioactivity remaining after wash. Measuring radioactivity in a sample may be performed by a number of methods known in the art. For example, the amount of radioactivity may be determined directly by counting each sample, using for example a scintillation counter. Samples may also be run on a polyacrylamide gel, the gel may be placed under x-ray film and a densitometric reading of the autoradiogram may be taken.

Assays are not limited to detecting binding affinity but may also detect other desired activities such as catalytic or enzymatic activity. Some embodiments of the present invention provide for detection of specific activity by a cell culture assay. For example, inhibition of cell adhesion may indicate binding of oligomer to a target molecule involved in cell adhesion. In further embodiments of the present invention further groups of sets are prepared. Each of said further groups have a selected number of sets of oligomers. Sets of further groups have in a previously defined common position, units appearing in the previously defined common position in previously selected set. Each set of the further sets has a different unit in an additional defined common position. The units in the positions of the oligomer that are not in a common position are randomized.

For example, in one group, the previously selected set may be comprised of an adenine in the previously defined common position. A further group may retain said adenine in said previously defined common position, and at another defined common position each set in said further group may be comprised of a different unit, either adenine, guanine, thymine or cytosine. The units in the positions of the oligomer that are not in a common position are randomized.

In further embodiments of the present invention, common positions are comprised of multiple oligomer positions as described above. For example, for a 9-mer, the one common position may be the third position of the 9-mer, or the common position may be comprised of the third position and the fourth position of the 9-mer.

Procedures useful for increasing the complexity of an oligomer group, and/or increasing specific activity of an oligomer described previously are equally applicable to said further groups. Thus, oligomer groups may be comprised of multiple units, may be sterically constrained and may be subfractionated prior to assaying for specific activity. Furthermore, oligomers of further groups may comprise one or more cassettes.

Sets are again assayed for desired activity. The steps described above may be performed iteratively.

The following examples are illustrative, but not limiting of the invention.

EXAMPLE 1

Synthesis of DNA Oligonucleotides

Unmodified DNA oligonucleotides are synthesized on an automated DNA synthesizer (Applied Biosystems model 380B) using standard phosphoramidite chemistry with oxidation by iodine. β-cyanoethyldiisopropyl phosphoramidites may be purchased from Applied Biosystems (Foster City, Calif.).

EXAMPLE 2

Synthesis of RNA Oligonucleotides

Unmodified RNA oligonucleotides having random base sequences were synthesized on an automated DNA synthesizer (Applied Biosystems model 380B) using modified standard phosphoramidite chemistry synthesis with oxidation by iodine. The standard synthesis was modified by increasing the wait step after the pulse delivery of tetrazole to 900 seconds. β-cyanoethyldiisopropyl phosphoramidites were purchased from Applied Biosystems (Foster City, Calif.). The bases were deprotected by incubation in methanolic ammonia overnight. Following base deprotection, the oligonucleotides were dried in vacuo. The t-butyldimethylsilyl protecting the 2' hydroxyl was removed by incubating the oligonucleotide in 1M tetrabutylammoniumfluoride in tetrahydrofuran overnight. The RNA oligonucleotides were further purified on $C_{18}$ Sep-Pak cartridges (Waters, Division of Millipore Corp., Milford, Mass.) and ethanol precipitated.

EXAMPLE 3

Synthesis of Phosphorothioate Oligonucleotides

Phosphorothioate oligonucleotides represent a class of oligonucleotide analog that is substantially nuclease resistant. Phosphorothioate RNA oligonucleotides and phosphorothioate DNA oligonucleotides were synthesized according to the procedure set forth in Examples I and 2 respectively, replacing the standard oxidation bottle by a 0.2M solution of 3H-1,2-benzodithiole-3-one 1,1-dioxide in acetonitrile for stepwise thiation of phosphite linkages. The thiation cycle wait step was increased to 68 seconds and is followed by the capping step.

EXAMPLE 4

Synthesis of 2'-O-alkyl Phosphorothioate Oligonucleotides

2'-O-methyl phosphorothioate oligonucleotides were synthesized according to the procedures set forth in Example 3 substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'-O-propyl, 2'-O-phenyl and 2'-O-nonyl phosphorothioate oligonucleotides may be prepared by slight modifications of this procedure.

EXAMPLE 5

Preparation of Pyrene Oligonucleotide Analogs

Oligonucleotides were prepared by incorporating 2' aminopentoxyadenosine at desired sites. The oligonucleotides were dissolved in 0.2M $NaHCO_3$ buffer and treated with 50 fold excess of N-hydroxysuccinimide ester of pyrene-1-butyric acid dissolved in dimethylformamide. The resultant mixture is incubated at 37° C. for 4–5 hours and the conjugate is purified by reverse phase HPLC followed by desalting in a G-25 Sephadex column.

EXAMPLE 6

Synthesis of Oligonucleotide Having Randomized Positions

Four columns of the DNA synthesizer were packed with a mixture containing an equal amount of adenosine(A)-, cytidine(C)-, guanosine(G)- and uracil(U)-controlled pore glass (CPG, Chemgenes, Needham, Mass.). At coupling steps where a given nucleotide base was desired, the defined phosphoramidite was delivered to each column. At each "random" coupling step, an equimolar mixture of all four phosphoramidites was delivered to each column.

EXAMPLE 7

Preparation of Radiolabeled Groups

Oligonucleotide groups prepared in accordance with Example 1 through 6 may be radiolabeled using [γ-$^{32}$P] ATP and T4 polynucleotide kinase as described in Maniatis, et al. "Molecular Cloning: A Laboratory Manual" (Cold Spring Harbor, N.Y.).

EXAMPLE 8

Effect of Site of Unrandomization on Activity

Twenty-four sets of phosphorothioate oligonucleotides were prepared in accordance with Examples 3 and 6 as set forth in Table 2.

TABLE 2

| Set 1 ANNNNN | Set 13 NNNANN |
|---|---|
| Set 2 CNNNNN | Set 14 NNNCNN |
| Set 3 GNNNNN | Set 15 NNNGNN |
| Set 4 TNNNNN | Set 16 NNNTNN |
| Set 5 NANNNN | Set 17 NNNNAN |
| Set 6 NCNNNN | Set 18 NNNNCN |
| Set 7 NGNNNN | Set 19 NNNNGN |
| Set 8 NTNNNN | Set 20 NNNNTN |
| Set 9 NNANNN | Set 21 NNNNNA |
| Set 10 NNCNNN | Set 22 NNNNNC |
| Set 11 NNGNNN | Set 23 NNNNNG |
| Set 12 NNTNNN | Set 24 NNNNNT |

Each of the sets is tested for activity against a target molecule to determine which order of unrandomization gives the highest initial specific activity.

EXAMPLE 9

Preparation of a Biotin Oligonucleotide Group

An oligonucleotide group having the sequence TNNNXNNNTB, wherein N is any of A, G, C, or U, X is one of A, G, C and U and B is biotin, is prepared in accordance with Examples 3 and 6. The sequence is designed with flanking thymidines to provide sites for radiolabeling. A control having the sequence TNNNX-NNNT is also prepared in accordance with Examples 3 and 6.

EXAMPLE 10

Preparation of Oligonucleotide Group comprising Nucleotide Analogs.

Oligonucleotide groups having the sequence NNNX-NNNU are prepared in accordance with Example 1 and 6 incorporating one or more of the nucleoside analogs 2'-O-nonyl adenosine, N6-imidazoylpropyl guanosine, 2'-O-aminopentyl cytidine, 2'-O-pentyl-adenosine, 2'-O-pentyl-guanosine, 2'-O-pentyl-cytidine, 3'-terminal 2'-O-methyl uridine and 6-amino-2-hydroxylmethyl-1-hexanol. The nucleosides, 2'-O-nonyl adenosine, N6-imidazoylpropyl guanosine, 2'-O-aminopentyl cytidine, 2'-O-pentyl-adenosine, 2'-O-pentyl-guanosine, 2'-O-pentyl-cytidine, 3'-terminal 2'-O-methyl uridine were prepared by modification of the methods described in PCT US91/00243 filed Jan. 11, 1991. 6-amino-2-hydroxylmethyl-l-hexanol is available commercially. The nucleosides are modified to provide the corresponding phosphoramidite by methods known to those skilled in the art.

EXAMPLE 11

Gel-shift Assay of Random 2-0-Methyl Oligonucleotlde Binding to ras RNA Target

The ras 47-mer stem/loop RNA was enzymatically synthesized, $^{32}$P end-labeled according to standard procedures, and gel-purified. 2'-O-Methyl oligonucleotide analog libraries comprising four sets were prepared in accordance with Examples 4 and 6. Each set was tested for binding against the RNA target and a "set $K_D$" was determined in accordance with the following procedure.

In a first round the ras RNA target was incubated at a concentration of approximately 10 pM with each of the four random 2'-O-methyl oligonucleotide sets, at concentrations of 5, 10, 50 and 100 µM in a buffer consisting of 100 mM NaCl and 10 mM MgCl$_2$. The hybridization was carried out for four hours at 37° C., followed by electrophoretic separation of bound vs. unbound material on a 20% acrylamide gel in Tris-Borate buffer (TBE) plus 50 mM NaCl, run at 25 W for four hours. The gel was dried and the radioactive bands were visualized on a phosphorimager (Molecular Dynamics). The ras stem/loop target alone is the lowest band visible on the gel (highest mobility). As this target binds oligonucleotide (non-radioactive), the mobility of the ras target is decreased, shifting the band to a higher position on the gel (complex). In FIG. 2A no binding is seen for the oligonucleotide sets NNNNGNNNN or NNNNUNNNN, but NNNNANNNN shows a slight shift at 100 uM and NNNNCNNNN shifts more than 50% of the target to the bound form at 50 uM oligonucleotide concentration.

Figure 2B:
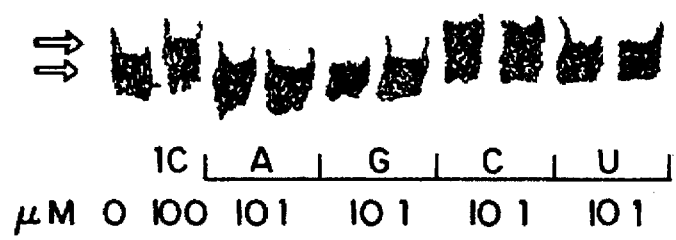
Figure 2C:
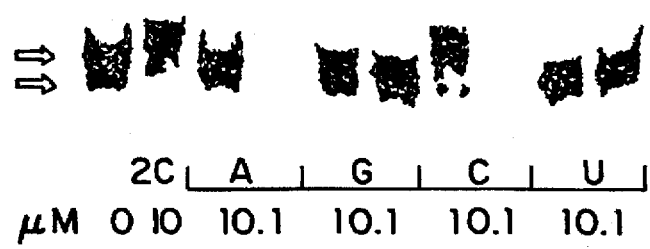

The protocol was then repeated in Round 2. The ras RNA target was incubated at a concentration of approximately 10 pM with each of the four random oligonucleotide sets synthesized according to the method described above, at concentrations of 1 and 10 µM to provide the gel image of FIG. 2B which shows that oligonucleotide sets NNNNCNANN, NNNNCNGNN and NNNNCNUNN show minimal binding. NNNNCNCNN shows a shift of more that 25% of the target at 1 µM and about 50% of the target at 10 µM. In Round 3 the ras RNA target was incubated with the random oligonucleotide sets at concentrations of 0.1 and 1 µM to provide the gel image of FIG. 2C where only NNCNCNCNN showed binding, exhibited by a shift of greater than 50% of the target.

Table 3 sets forth results of nine rounds performed to determine the "winner" sequence which binds to the ras RNA target. $K_D$ are in µM.

TABLE 3

| Round | Sequence* | Q** | $K_D$ | | | |
|---|---|---|---|---|---|---|
| | | | A | C | G | U |
| 1 | NNNNXNNNN | 65,536 | 22 | 10 | >100 | >100 |
| 2 | NNNNCNXNN | 16,384 | >10 | 4 | >10 | >10 |
| 3 | NNXNCNCNN | 4,096 | >10 | 0.5 | >10 | >10 |
| 4 | NNCXCNCNN | 1,024 | >10 | 0.15 | >10 | >10 |
| 5 | NNCCCXCNN | 256 | 0.08 | >1 | 0.4 | >1 |
| 6 | NNCCCACXN | 64 | 0.05 | >0.5 | 0.08 | >0.5 |
| 7 | NXCCCACAN | 16 | >0.1 | >0.1 | 0.03 | >0.1 |
| 8 | NGCCCACAX | 4 | 0.05 | 0.02 | 0.05 | 0.042 |
| 9 | XGCCCACAC | 1 | 0.03 | 0.05 | 0.02 | 0.01 |

*wherein N is any of A, C, G or T;
**Q is set complexity.

As illustrated in Table 3, it was not difficult to distinguish the set with the lowest $K_D$ (µM) at each round of synthesis and screening.

As expected for oligonucleotide hybridization reactions, positions near the center of the oligonucleotide had a greater effect on the $K_D$ than positions on the extreme 5' or 3' ends. For example, an attempt to fix the 3' position in round 4 did not yield results that distinguished the sets. An alternative position was selected for round 4 which yielded a clear winner, and then the sequence was elucidated from the center of the oligomer to the ends. The final oligonucleotide selected by the procedure is complementary to the single stranded loop region of the target RNA.

EXAMPLE 12

ELISA for Detection of Inhibition of Herpes Simplex Virus-1

ELISA for detection of HSV-1 envelope glycoprotein B (gB) was performed by infection of normal dermal fibroblast cells (NHDF, Clonetics) with HSV-1 (KOS) at a multiplicity of infection of 0.05 PFU/cell. Following virus adsorption, cells were washed and treated with growth media containing oligoeucleotide. Oligonucleotides were tested in triplicate wells at four concentrations. Cells were fixed 48 hours postinfection and assayed for the presence of HSV-1 gB antigen by ELISA. Standard deviation were typically within 10%.

EXAMPLE 13

Inhibition of Herpes Simplex Virus-1 Activity by Phosphorothioate Oligonucleotide Sets A group of 65,536 unique 8-mers in 4 sets of 16,348 was prepared in accordance with Examples 3 and 6 each was screened for activity against human herpes simplex virus type 1 (HSV-1) in cell culture in accordance with the procedure described in Example 12. As illustrated in Table 4, antiviral activity was observed with increasing potency at each round of synthesis and screening, with no difficulty discerning the most active set (in bold) in each round.

TABLE 4

| Round | Sequence* | Q** | IC$_{50}$ (µM) when × = | | | |
|---|---|---|---|---|---|---|
| | | | A | C | G | T |
| 1 | NNNXNNNN | 16,348 | >100 | >100 | 70 | >100 |
| 2 | NNNGNNNX | 4,096 | >100 | >100 | 30 | >100 |
| 3 | NNNGNXNG | 1,024 | >100 | >100 | 15 | >100 |
| 4 | NXNGNGNG | 256 | 30 | 30 | 5 | 20 |
| 5 | XGNGNGNG | 64 | 20 | 20 | 1.5 | 20 |
| 6 | GGNGXGNG | 16 | 10 | 10 | 1.5 | 10 |
| 7 | GGXGGGNG | 4 | 1.3 | 1.3 | 0.5 | 1.3 |
| 8 | GGGGGGXG | 1 | 0.7 | 0.7 | 1.1 | 0.4 |

*where N is any of A, C, G or T;
**where Q is set complexity.

The oligonucleotide set containing a fixed guanine had the most activity in every round of HSV screening except the last round, resulting in selection of a guanine at nearly all fixed positions.

EXAMPLE 14

Optimization of G4 Core Containing 8-met oligonucleotide for HSV-1 Antiviral Activity To determine the optimal 8:met containing a $G_4$ core, a oligonucleotide group was designed as shown in Table 5, using the oligonucleotide cassette GGGG.

TABLE 5

| Sequence* | Most Active × = | IC$_{50}$ (µM) |
|---|---|---|
| NNGGGGNX | A | 2.5 |
| NNGGGGXA | T | 1.1 |
| XNGGGGTA | G | 0.8 |
| GXGGGGTA | C | 0.8 |

*N is any of A, G, T or C.

As shown in Table 5, optimization of the sequences surrounding the $G_4$ core produced a 3 fold increase in antiviral activity in four rounds of synthesis and screening, suggesting that although the $G_4$ core is the most important component of the activity, potency can be modulated by the flanking sequences.

EXAMPLE 15

Assay for Detection of Inhibition of Human Immunodeficiency Virus

The human T-lymphoblastoid CEM cell line was maintained in an exponential growth phase in RPMI 1640 with 10% fetal calf serum, glutamine, and antibiotics. On the day of the assay, the cells were washed and counted by trypan blue exclusion. These cells (CEM-IIIB) were seeded in each well of a 96-well microtiter plate at $5 \times 10^3$ cells per well. Following the addition of cells to each well, the compounds were added at the indicated concentrations and serial half log dilutions. Infectious HIV-$1_{IIIB}$ was immediately added to each well at a multiplicity of infection determined to give complete cell killing at 6 days post-infection. Following 6 days of incubation at 37° C., an aliquot of supernatant was removed from each well prior to the addition of the tetrazolium dye XTT to each well. The XTT was metabolized to a formazan blue product by viable cells which was quantitatively measure spectrophotometrically with a Molecular Devices Vmax Plate Reader. The XTT assay measures protection from the HIV-induced cell killing as a result of the addition of test compounds. The supernatant aliquot was utilized to confirm the activities determined in the XTT assay. Reverse transcriptase assays and p24 ELISA were performed to measure the amount of HIV released from the infected cells. Protection from killing results in an increased optical density in the XTT assay and reduced levels of viral reverse transcriptase and p24 core protein.

EXAMPLE 16

Inhibition of Human Immunodeficiency Virus by Phosphorothioate Oligonucleotide Sets A group of 65,536 unique 8-mers in 4 sets of 16,348 each were prepared in accordance with Examples 3 and 6 and screened for activity in accordance with Example 12. The compound sets are described in Table 6. Table 6 sets forth the $IC_{50}$ (µM) for four oligonucleotide sets.

TABLE 6

| Set | Sequence* | IC$_{50}$ (µM) |
|---|---|---|
| A | NNNN A NNN | inactive |
| B | NNNN C NNN | inactive |
| C | NNNN G NNN | 5 |
| D | NNNN T NNN | inactive |

*where N is any of A, C, G, or T.

Set C sowed 50% inhibition of HIV-induced cytopathic effects at 5 µM, while the other compound sets were inactive at concentration up to 25 µM.

EXAMPLE 17

Assay for the Detection of Inhibition of Cytomegalovirus

Confluent monolayer cultures of human dermal fibroblasts were treated with oligonucleotide sets at the indicated concentrations in serum-free fibroblast growth media. After overnight incubation at 37° C., culture medium containing oligonucleotide was removed, cells were rinsed and human cytomegalovirus was added at a multiplicity of infection of 0.1 pfu/cell. After a 2 hour adsorption at 37° C., virus was removed and fresh fibroblast growth medium containing oligonucleotide sets at the indicated concentrations was added. Two days after infection, old culture medium was removed and replaced with fresh fibroblast growth medium containing oligonucleotide sets at the indicated concentrations. Six days after infection media was removed, and cells fixed by addition of 95% ethanol. HCMV antigen expression was quantitated using an enzyme linked immunoassay. Primary reactive antibody in the assay was a monoclonal antibody specific for a late HCMV viral protein. Detection was achieved using biotinylated goat anti-mouse IgG as secondary antibody followed by reaction with streptavidin conjugated B-galactosidase. Color was developed by addition of chlorophenol red B-D-galactopyranoside and absorbance at 575 nanometers measured using an ELISA plate reader. Results are expressed as percent of untreated control and were calculated as follows:

$$\% \text{ Control} = 100 \times \frac{\text{infected cell control} - \text{treated cells}}{\text{infected cell control} - \text{unifected cell control}}$$

EXAMPLE 18

Inhibition of Cytomegalovirus by Phosphorothioate Oligonucleotide Sets

Figure 3:
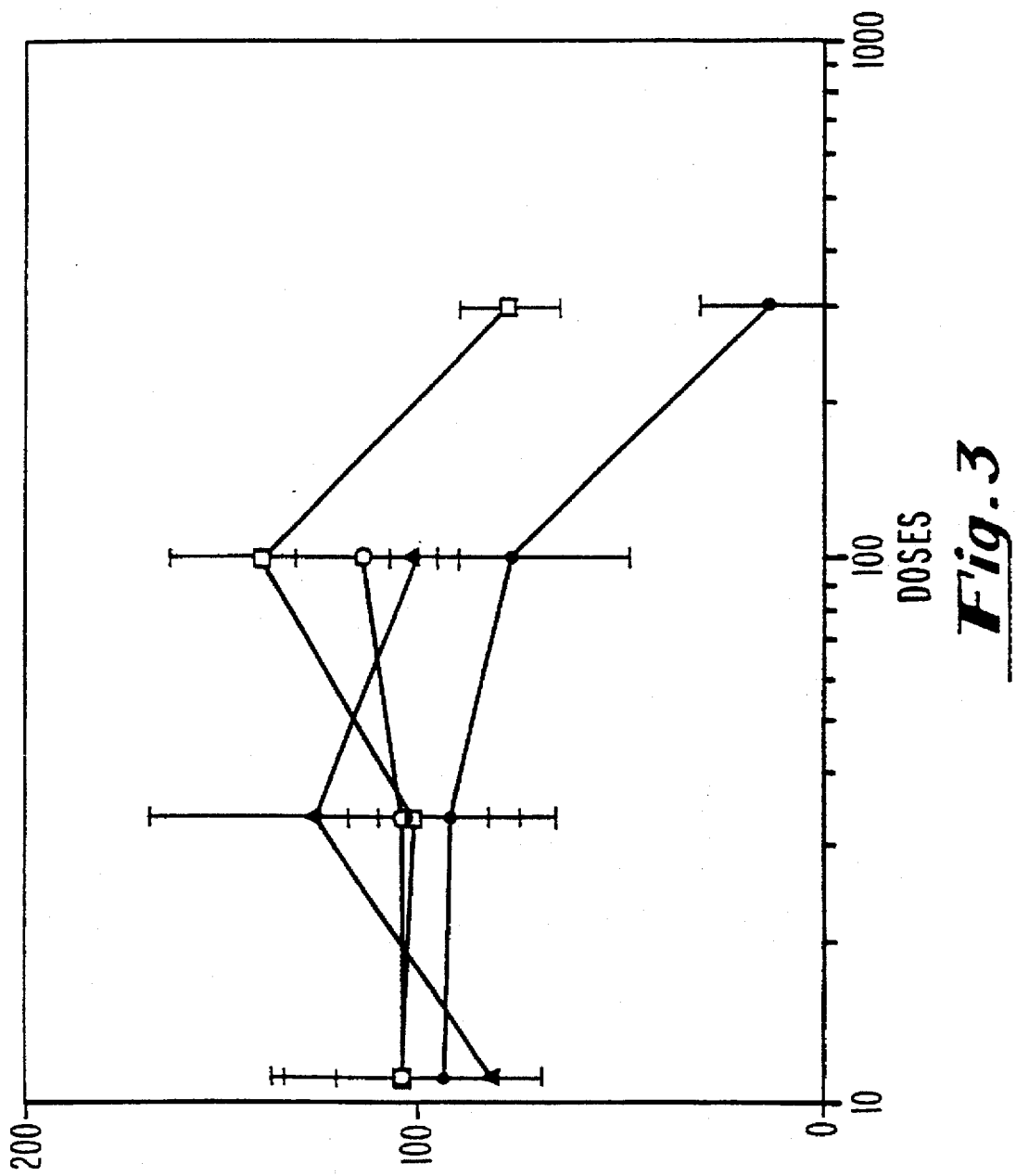
FIG. 3 is a schematic representation of inhibition of cytomegalovirus activity by four different oligonucleotide sets. Compound set C had the greatest activity against cytomegalovirus

A group of 65,536 unique phosphorothioate 8-mers in 4 sets of 16,438 were prepared in accordance with Examples 3 and 6 and screened for activity against the human cytomegalovirus in accordance with Example 14. The compound sets A (NNNNANNN), B (NNNNGNNN), C (NNNNCNNN) and D (NNNNTNNN), where N is any of A, G, C or T, were screened at a range of concentration from 10 to 200 µM. The results shown in FIG. 3 show that compound set B had the greatest activity against cytomegalovirus, causing approximately 20% inhibition at a 100 µM dose and 90% inhibition at a 200 µM dose. Sets A, B and D exhibited minimal to no antiviral activity.

EXAMPLE 19

Assay to Detect Inhibition of Influenza A Virus

Vero cells were pretreated overnight with randomer sets by direct addition to the-media at 10 µM and 100 µM concentrations. After overnight treatment cells were infected with influenza A/PR/8 at a MOI of 0.05. Following infection cells were incubated for 48 hours in the presence of oligonucleotide. After incubation cells were fixed with methanol and air dried. Monolayers were then assayed by ELISA for matrix protein. Primary antibody was a monoclonal antibody specific for matrix protein of influenza A virus (B020 Bioproducts for Science). Second antibody was goat anti-mouse IgG conjugated to alkaline phosphatase (BRL, Bethesda, Md.). Substrate was ATTO-PHOS reagent, JBL. Fluorescence was measured using a Millipore Cytofluour 2300 with excitation at 450 nM and emission read at 580 nM.

EXAMPLE 20

Inhibition of Influenza Virus by Phosphorothioate Oligonucleotide Sets

Figure 4:
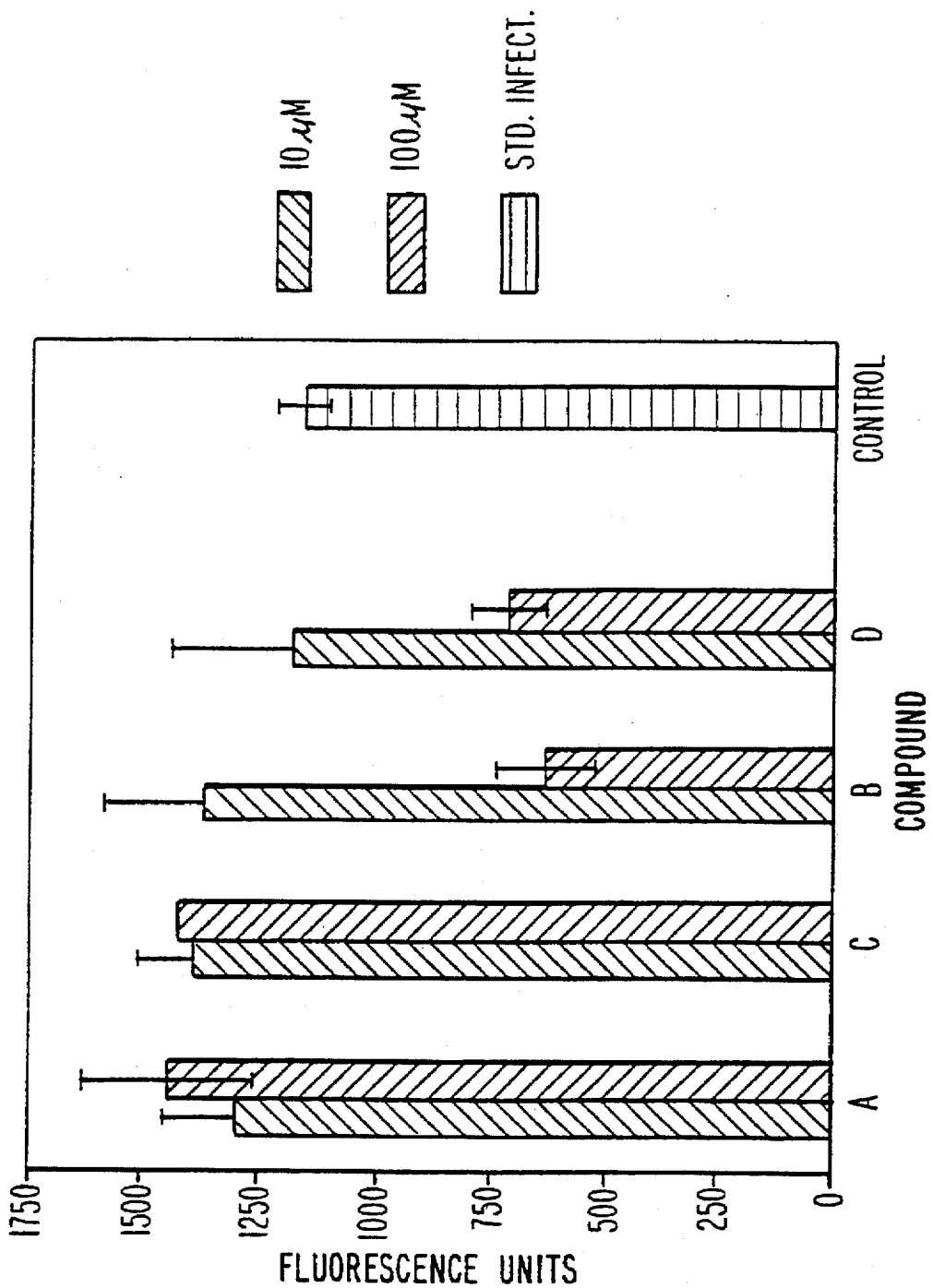
FIG. 4 is a schematic representation of inhibition of influenza virus activity caused by four different oligonucleotide sets at concentration of 10 μM and 100 μM of oligonucleotide. Compound sets B and D had the greatest antiviral activities.

A group of 65,536 unique phosphorothioate 8-mers in 4 sets of 16,438 was prepared in accordance with Examples 3 and 6 and was screened for activity against the Influenza A virus as described in Example 16. The compound sets A (NNNNANNN), B (NNNNGNNN), C (NNNNCNNN) and D (NNNNTNNN), where N is any of A, G, C or T, were screened at 10 µM and 100 µM. The results as shown in FIG. 4 show that sets C and D had the greatest antiviral activities, set C exhibited approximately 50% inhibition and set D exhibited approximately 35% inhibition of viral activity. A and B exhibited minimal activity.

Data are the arithmetic mean and standard error of triplicate data points of a single experiment.

EXAMPLE 21

Determination of Oligonucleotides which Induce Interferon

A phosphorothioate oligonucleotide group comprising 20 sets having the sequence N N N N X N N N where N is any of adenine, guanine, cytosine or thymidine and X is one of adenins, guanine, cytosine or thymidine is prepared in accordance with Examples 3 and 6. The sets are set forth in Table 7.

TABLE 7

| Set | Modification |
| --- | --- |
| 1–4 | natural |
| 5–8 | 2'-O-methyl |
| 9–12 | 2'-O-propyl |
| 13–16 | 2'-O-pentyl |
| 17–20 | 2'-O-nonyl |

An ELISA is performed to determine the set which is most effective to induce interferon. The nucleotide in the most effective set is fixed and sets having the fifth position fixed and the fourth position one of adenine, guanine, cytosine or thymidine is prepared. An ELISA is performed to determine the set which is most effective to induce interferon. The steps are repeated until all of the positions are determined.

EXAMPLE 22

Gel Shift Assay of Random Pyrene Oligonucleotide Sets Binding to HIV TAR Element The HIV TAR element is a structured RNA found on the 5'-end of all HIV transcripts. A gel shift has been used to analyze the binding of four oligonucleotide sets to the HIV TAR element (illustrated in FIG. 5A). The target RNA has a three base bulge that is required for binding of the transcriptional activation protein tat. The oligonucleotides set forth in Table 8 were prepared in accordance with Examples 5 and 6, each containing a pyrene analog (indicated by A*).

TABLE 8

| | | SEQ-ID NO: |
| --- | --- | --- |
| SET 1 | N N N A* N A N N N N | 3 |
| SET 2 | N N N A* N C N N N N | 4 |
| SET 3 | N N N A* N G N N N N | 2 |
| SET 4 | N N N A* N U N N N N | 5 |

Figures 5A, 5B, 6:
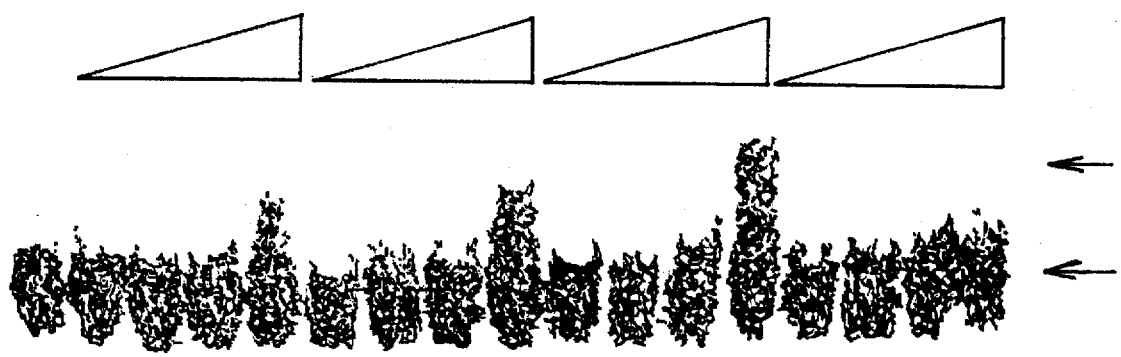
FIG. 5A is a schematic representation of the nucleotide sequence and secondary structure of the HIV TAR element (SEQ ID NO:20).
FIG. 5B is a representation of a gel image showing binding affinity of four oligonucleotide sets for the HIV TAR element at four different oligonucleotide concentrations. The oligonucleotide set NNNA'NGNNNN (SEQ ID NO:2) had the greatest binding affinity.
FIG. 6 is a schematic representation of the nucleotide sequence and secondary structure of the HIV gag-pol stem loop (SEQ ID NO:21).

The assay uses a 15 pM concentration of the radioactively labeled target and an 0.1, 1, 10, and 100 µM concentrations of each set. Binding of molecules from the set to the target results in a slower mobility complex. Set 3 binds best to TAR as illustrated in FIG. 5B wherein 100 µM of the oligonucleotide set caused a shift of approximately 50% of the target. 100 µm of the oligonucleotide set 2 caused a shift of approximately 25% of the target. Sets 1 and 4 caused minimal shift of the target. The sixth position will be fixed as a G and another position unrandomized in the second round of synthesis and assays.

EXAMPLE 23

Random Oligonucleotide Set Binding to HIV gag-pol Triple Strand

Binding to double stranded DNA or RNA is possible by formation of a three stranded complex with the incoming third strand binding in the major groove of the duplex RNA or DNA. The molecular nature of the interaction between the oligomer and target need not be known in order to practice the technique. Thus, it is possible that novel interactions between oligomers and DNA or RNA will be responsible for binding. FIG. 6 illustrates a double stranded RNA structure from HIV known as the gag-pol stem loop (Vickers and Ecker, Nucleic Acids Research). One of the limitations in the design of triple strand interactions is the need to have a long stretch of homopurines as a target. The 3' (right) side of the gag-pol stem loop is homopurine except for a pair of cytosines near the bottom of the stem. To determine the best oligonucleotide to bind to the gag-pol stem loop, a group of RNA oligonucleotide sets was designed to bind to the purine-rich strand of the gag-pol stem-loop by Hoogstein base pairing and prepared in accordance with Examples 2 and 6. At the position of the two cytosines the sequence was randomized to provide the sequences set forth in Table 9. Binding to the gag-pol stemloop was measured by gel shift analysis as previously described in Example 8 with the following modifications: the radiolabeled gag-pol RNA was incubated with the oligonucleotide in 100 mM NaCl, 25 mM TRIS acetate pH5, 2 mM Mg Cl$_2$, 1 mM spermidine. The gel was a 15% acrylamide with 50 mM NaCl$_2$ mM MgCl$_2$ added to the running buffer.

The results in Table 9 show that in round 1 the oligonucleotide set CCCUUCCCNUC (SEQ ID NO: 8) had the greatest affinity for the target with a K$_D$ of 50. In the second round the C was fixed in the eighth position and the ninth position was determined. The oligonucleotide CCCUUCCCCUC (SEQ ID NO: 12) had the greatest affinity for the target in the ninth round with a K$_D$ of 1. Thus, a triple strand-binding sequence can be optimized.

TABLE 9

| Set | Sequence | K$_D$ (µM) | SEQ ID NO: |
| --- | --- | --- | --- |
| Round 1 | | | |
| A$_1$ | CCCUUCCANUC | >100 | 6 |
| B$_1$ | CCCUUCCGNUC | >100 | 7 |
| C$_1$ | CCCUUCCCNUC | 50 | 8 |
| D$_1$ | CCCUUCCUNUC | 100 | 9 |
| Round 2 | | | |
| A$_2$ | CCCUUCCCAUC | 10 | 10 |
| B$_2$ | CCCUUCCCGUC | 1.0 | 11 |
| C$_2$ | CCCUUCCCCUC | 1 | 12 |
| D$_2$ | CCCUUCCCUUC | 10 | 13 |

EXAMPLE 24

Random Oligonucleotide Binding to Transcription Factors

A radiolabeled oligonucleotide group was prepared having the sequence NNGGGGNX wherein N is any of A, G, T or C and X is one or A, G, T or C as described in Examples 3, 6 and 7. The group was screened for binding to the HIV tat protein, which is a transcription factor produced by the virus as described in Example 24. Binding activity was observed.

EXAMPLE 25

Random 2'-O-Methyl Oligonucleotide Binding to Endothelin-1

Receptor and radiolabeled ligand were supplied in a kit obtained from DuPont/NEN. Assays were performed according to the manufacturer's instructions. A random 2'-O-methyl group was prepared in accordance with Examples 4 and 6 to provide four sets having the sequences GCGNNNANNNNNNCGC (SEQ ID NO: 14); GCGNNNGNNNNNNCGC (SEQ ID NO:15); GCGNNNCNNNNNNCGC (SEQ ID NO:16); GCGNNNUNNNNNNCGC (SEQ ID NO: 17) where N is any of A, G, C or U. Each set was diluted to 100 µM in an assay buffer provided in the kit, then incubated with the receptor and ligand as per the manufacturer's protocol. Following the incubation, ligand- bound receptor was separated from unbound by vacuum filtration through glass filters. The bound ligand was then eluted from the filter in scintilation fluid and counted in a scintilation counter. Receptor and ligand were incubated with an excess of unlabeled ligand in order to establish the level of non-specific binding (NSB) to the filters and with no oligonucleotide set (zero) to establish the level of complete binding.

The results shown in Table 10 indicate that set B was most active against Endothelin-1.

TABLE 10

|  | CPM | NET CPM | % I |
| --- | --- | --- | --- |
| NSB | 284 | — | — |
| zero | 1421 | 1140 | 100 |
| A | 1223 | 939 | 82 |
| B | 1200 | 916 | 80 |
| C | 1347 | 1063 | 93 |
| D | 1330 | 1046 | 92 |

EXAMPLE 26

Random 2'-O-Methyl Oligonucleotide Binding to Leukotriene B4

Receptor and radiolabeled ligand were supplied in a kit obtained from DuPont/NEN. Assays were performed according to the manufacturer's instructions. A random 2'-O-methyl group was prepared in accordance with Examples 4 and 6 to provide four sets having the sequences GCGNNNANNNNNNCGC (SEQ ID NO: 14); GCGNNNGNNNNNNCGC (SEQ ID NO:15); GCGNNNCNNNNNNCGC (SEQ ID NO:16); GCGNNNUNNNNNNCGC (SEQ ID NO: 17) where N is any of A, G, C or U. Each set was diluted to 100 µM in an assay buffer provided in the kit, then incubated with the receptor and ligand as per the manufacturer's protocol. Following the incubation, ligand- bound receptor was separated from unbound by vacuum filtration through glass filters. The bound ligand was then eluted from the filter in scintilation fluid and counted in a scintilation counter. Receptor and ligand were incubated with an excess of unlabeled ligand in order to establish the level of non-specific binding (NSB) to the filters and with no oligonucleotide set (zero) to establish the level of complete binding. The results shown in Table 11 indicate that set D was most active against leukotriene B4.

TABLE 11

|  | CPM | NET CPM | % I |
| --- | --- | --- | --- |
| NSB | 383 | — | — |
| zero | 1063 | 680 | 100 |

TABLE 11-continued

|  | CPM | NET CPM | % I |
| --- | --- | --- | --- |
| A | 989 | 606 | 89 |
| B | 953 | 570 | 84 |
| C | 900 | 517 | 76 |
| D | 894 | 511 | 75 |

EXAMPLE 27

Phosphorothioate and 2'-O-Methyl Oligonucleotide Binding to the Vital Receptors CD4

Two groups of oligonucleotides were prepared. A phosphorothioate oligonucleotide group was prepared in accordance with Examples 3 and 6. A 2'-O-methyl oligonucleotide group was prepared in accordance with Examples 4 and 6. Both groups have the sequence NNNNTNNNN where N is any of A, C, G or T.

Figure 7:
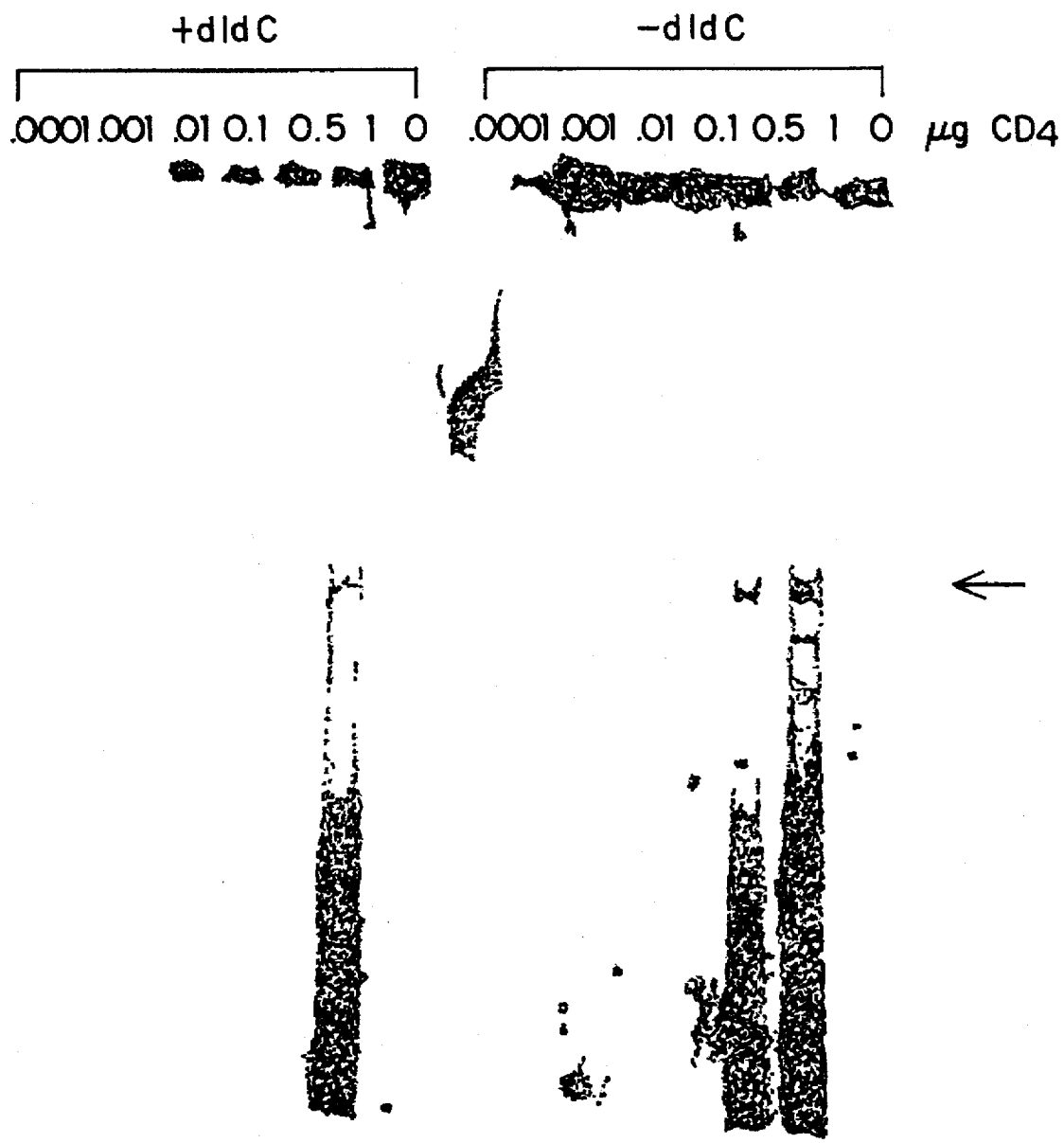
FIG. 7 is a representing of a gel image showing the binding affinity of 100 pmoles of a phosphorothioate oligonucleotide set having the sequence NNNNTNNNN for the protein CD4 in the presence and absence of a competitor, dIdC. 100 pmoles exhibited binding which was visible at 0.5 and 1 μG CD4.

100 pmoles of each group of random oligonucleotides is 5' end labeled to high specific activity with [$\gamma$-$^{32}$P] ATP and T4 polynucleotide kinase. Each labeled group is reacted with the protein CD4 at room temperature in a buffer consisting of 100 mM KCl, 1.5 mM mgCl$_2$, 0.2 mM EDTA, 10% glycerol, 1 mM DTT, and 20 mM HEPES (pH=7.9). poly dI•dC is added as indicated as a non-specific competitor. After 1 hour protein bound oligonucleotide is separated from unbound by electrophoresis on a 6% native acrylamide gel in 1X TBE buffer. The results of the phosphorothioate oligonucleotide assay is shown in FIG. 7 and indicates binding of the oligonucleotide to the protein (at the arrow). No binding has was detected by the 2'-O-methyl set. Binding has been observed with the phosphorothioate pool against the tat protein.

EXAMPLE 28

Preparation of Random Group of Polypeptides and Assay for Binding Thereof

Polypeptides may be used in the practice of this invention. Monomer amino acids are easily oligomerized into peptides using the appropriate precursor chemicals and instruments available to those skilled in the art, such as those that can be purchased from Applied Biosystems.

The first round of synthesis is as follows:

TABLE 12

| Position | 1 | 2 | 3 | 4 | 5 | 6 | 7 | 8 | 9 |
| --- | --- | --- | --- | --- | --- | --- | --- | --- | --- |
| Set 1 | X | X | X | X | B | X | X | X | X |
| Set 2 | X | X | X | X | A | X | X | X | X |
| Set 3 | X | X | X | X | W | X | X | X | X |
| Set 4 | X | X | X | X | L | X | X | X | X | where A is defined as an acidic amino acid, B is defined as a basic amino acid, W is defined as a neutral amino acid, L is defined as a lipophilic amino acid, and X is defined as any amino acid from the above identified group.

Each of the above sets is tested for inhibition of cell adhesion using a cell culture assay in which the ICAM-1 mediated binding of cells is measured as described. Dustin, M. L. and Springer, T. A. J. *Cell Biol.* 1988, 107, 321. The set showing greatest inhibition of cell adhesion at the lowest polypeptide concentration is selected.

The protocol is repeated, retaining the selected amino acid at position 5, and sequentially testing each remaining position to reach an optimal binding sequence.

EXAMPLE 29

Figure 8:
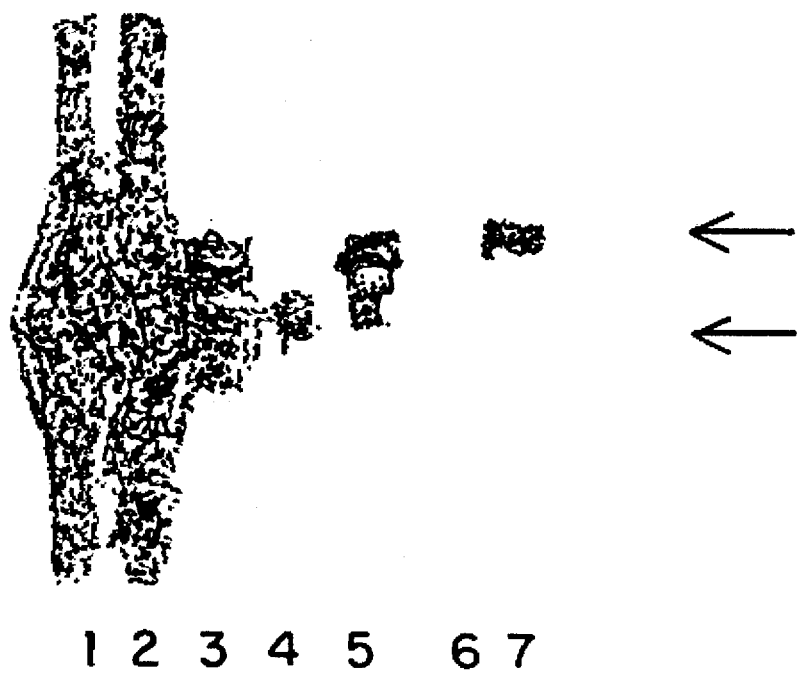
FIG. 8 is a representation of a gel image showing selection of an oligonucleotide with the highest affinity for a biotinylated target oligonucleotide. The "winner" sequence (top arrow) was evident through three rounds of the procedure. Lane 1 is the input material diluted 1:10. Lane 2 is the supernatant diluted 1:10. Lane 3 is the bound material. Lanes 4 and 5 are the supernatant (1:10 dilution) and bound material of round 2, respectively. Lanes 6 and 7 are the supernatant (1:10 dilution) and bound material or round 3, respectively. The top arrow indicates "winner" material. Randomer library material migrates to the position indicated by the bottom arrow.

Identification of Oligonucleotide Sequence Using Streptavidin Capture of Biotinylated Target 0.2 µM of a target oligonucleotide having the sequence 3'dBAB AGA CGT CTT GCG 5' (SEQ ID NO: 18) wherein B is biotin, was incubated for 30 minutes at room temperature with 10 µM of a radiolabeled 2'-O-methyl oligonucleotide group prepared in accordance with Examples 4, 6 and 7 having the sequence NNN NCN CNN wherein N is any of adenine, cytosine, thymidine or guanine, and 0.1 µM of a radioactively labeled oligonucleotide complementary to the target (dTCTGCAGAACGC; SEQ ID NO: 19). The target oligonucleotide and any bound radioactively labeled oligonucleotide was captured on streptavidin-coated magnasphere beads (Promega), the beads were washed, and supernatant removed. The captured radioactively labeled oligonucleotide was removed from the beads and run on a polyacrylamide gel. FIG. 8 sets forth a sample gel which indicates that a "winner" can be separated from an excess of random sequence oligonucleotides. The procedure was repeated. In lane i was run a 1:10 dilution of the original solution prior to capture. Lane 2 is the supernatant diluted 1:10. Lane 3 is the bound material from the first round. A band of "winner" sequence is apparent, migrating to the first arrow. Lanes 4 and 5 are the supernatant (1:10 dilution) and bound material from the second round, respectively. The second round results in a "winner" band of greater purity. Lanes 6 and 7 are the supernatant (1:10 dilution) and bound material from the third round, respectively. The supernatant does not contain any radiolabeled oligonucleotides. The third round results in a "winner" band with little to no non-specific oligonucleotide.

EXAMPLE 30

Identification of a Protein Target

A group of oligonucleotides having the sequence NNNNNNNN wherein N is any one of adenine, guanine, thymidine or cytosine is prepared in accordance with Examples 3 and 6. The group is labeled using [γ-$^{32}$P] ATP and T4 polynucleotide kinase.

In individual wells of a 96-well nitrocellulose filter manifold, the following proteins are incubated in a solution of phosphate buffer saline: plasminogen activator $A_2$, tumor necrosis factor α, tumor necrosis factor β and gp120. Phosphate buffer saline only is added to a control well. The filter is washed. An aliquot of the labeled group of oligonucleotides is added to each well and incubated at room temperature for 10 minutes. The filter is washed and the counts in each well over background are counted to determine whether binding of the oligonucleotide to the protein occurred.

EXAMPLE 31

Determination of Phosphorothioate Oligonuclectide Having Binding Affinity for Nitrocellulose Bound Proteins An oligonucleotide analog group comprising four sets of oligonucleotides eight positions in length is prepared in accordance with Examples 3 and 6 and each set is tested for binding against the nitrocellulose-bound proteins identified in accordance with Example 27. The set having the highest affinity for each protein, as indicated by counts per well is the "winner set" for each protein. Results of the first round are as set forth in Table 13.

TABLE 13

| Position | 1 | 2 | 3 | 4 | 5 | 6 | 7 | 8 | Protein winner |
|---|---|---|---|---|---|---|---|---|---|
| Set 1 | N | N | N | N | A | N | N | N | plasminogen activator $A_2$, tumor necrosis factor α |
| Set 2 | N | N | N | N | G | N | N | N | no winner |
| Set 3 | N | N | N | N | C | N | N | N | gp120 |
| Set 4 | N | N | N | N | T | N | N | N | tumor necrosis factor β |

The filter is washed and wells counted. In a second round, the A is fixed in the fifth position and the sets (NNNAANNN), (NNNGANNN), (NNNCANNN), and (NNNTANNN) are prepared for testing in the wells containing plasminogen activator $A_2$ and tumor necrosis factor α. Similarly, sets in which the C is fixed in the 5th position or a T is fixed in the 5th position are prepared for testing in the gp120 and tumor necrosis factor β wells, respectively. By the eight round, "winner" sequences for all four target proteins are determined.

EXAMPLE 32

Determination of an Oligonucleotide Having Binding Affinity for a Target Protein using Subfractionated Sets of Oligonucleotides An oligonucleotide analog group comprising four sets of oligonucleotides eight positions in length is prepared in accordance with Examples 3 and 6 wherein each of the sets has a different one of adenins, guanine, thymidine and cytosine in the 5th position, and the rest of the positions are randomized to provide the group: NNNNANNN, NNNNGNNN, NNNNTNNN, and NNNNCNNN. Each set is subfractionated by charge with an anion exchange column. Each subfraction is tested for affinity for the target protein by gel shift assay. The subfraction from the set having an adenine in the 5th position has the highest binding affinity. In a further round, the 5th position is fixed to contain an adenins in the 5th position, and each set has a different nucleotide in the fourth position to provide the group NNNAANNN, NNNTANNN, NNNGANNN, and NNNCANNN. The sets are again subfractionated by charge with an anion exchange column and the subfractions are tested for affinity for the target protein by gel shift assay. The steps are repeated until each position is determined.

What is claimed is:

1. A method for determining an oligonucleotide having specific, assayable activity for a target comprising the steps of:
  (a) preparing a group of sets of oligonucleotides each oligonucleotide comprising at least four nucleotide units by:
    (i) defining a common position in the oligonucleotides of the sets, and
    (ii) synthesizing said sets of oligonucleotides such that each set has a different base unit in said common position, the base units which are not in said common position being randomized;
  (b) assaying each of the sets for activity against the target;
  (c) selecting a set based upon its activity against the target;
  (d) preparing a further group of sets of oligonucleotides, each of the sets of said further group of sets having in the previously defined common position the base unit appearing in that position in the set selected in step (c); each set of said further group of sets having a different base unit in an additional, defined common position, the base units in the positions of the oligonucleotides which are not in a defined common position being randomized;
  (e) assaying each of the sets of said further group of sets specific activity for the target;
  (f) selecting a set based upon its activity in said assay; and
  (g) performing steps (d), (e) and (f) iteratively until all positions of said oligonucleotide are identified, thereby determining an oligonucleotide having said specific assayable activity.

2. The method of claim 1 wherein said group is comprised of from about three to about twenty sets.

3. The method of claim 1 wherein said group is comprised of four sets.

4. The method of claim 1 wherein said oligonucleotides are from 4 to about 20 nucleotide units in length.

5. The method of claim 1 wherein said group of sets of oligonucleotides is labeled with a delectable label.

6. The method of claim 5 wherein the group of sets of oligonucleotides is radiolabelled.

7. The method of claim 1 wherein said assay is streptavidin capture of biotinylated target, filter binding assay or affinity chromatography.

8. The method of claim 1 wherein the group of sets of oligonucleotides are sterically constrained.

9. The method of claim 1 wherein said target a nucleic acid.

10. The method of claim 1 wherein said target is a carbohydrate.

11. The method of claim 1 wherein said target is a protein.

12. The method of claim 1 wherein said target is a glycoprotein.

13. The method of claim 1 wherein the target is an immunoglobulin, receptor, receptor binding ligand, antigen, enzyme, or transcription factor.

14. The method of claim 1 wherein the target is a phospholipase, tumor necrosis factor, endotoxin, interleukin, leukotriene, plasminogen activator, protein kinase, lipoxygenase, hydrolase, transacylase, or transcription factor.

15. The method of claim 1 wherein the target is a region of Epstein-Barr virus, rhinovirus, hepatitis virus, or influenza virus.

16. The method of claim 1 wherein the target is an RNA molecule or fragment thereof.

17. The method of claim 1 wherein the target is a region of a human immunodeficiency virus.

18. The method of claim 1 wherein the target is the TAR element of human immunodeficiency virus.

19. The method of claim 1 wherein the target is the gag-pol stem loop of human immunodeficiency virus.

20. The method of claim 1 wherein the target is the ras 47 base pair stem loop.

21. The method of claim 1 wherein the target is a region of a herpes virus.

22. The method of claim 1 wherein the target is a region of cytomegalovirus.

23. The method of claim 1 wherein the target is a region of an influenza virus.

24. The method of claim 1 wherein the target is endothelin-1.

25. The method of claim 1 wherein the target is leukotriene B-4.

26. The method of claim 1 wherein the target is human immunodeficiency virus gp 120.

27. The method of claim 1 wherein the target is the HIV tat protein.

28. The method of claim 1 wherein said assay is a gel shift assay.

29. The method of claim 1 wherein the target is a cell adhesion molecule.

30. The method of claim 1 wherein the target is a region of Candida, papiliomavirus, human immunodeficiency virus, herpes simplex virus or cytomegalovirus.

31. A method for determining an oligonucleotide cassette having specific, assayable activity for a target comprising the steps of:
  (a) preparing a group of sets of oligonucleotides, each oligonucleotide comprising at least four base units by:
    (i) defining a common position in the oligonucleotides of the sets, and
    (ii) synthesizing said sets of oligonucleotides such that each set has a different base unit in said common position, the base units which are not in said common position being randomized;

(b) assaying each of the sets for activity against the target;

(c) selecting a set based upon its activity in said assay;

(d) preparing a further group of sets of oligonucleotides, each of the sets of said further group of sets having in the previously defined common position the base unit appearing in the previously defined common position in the previously selected set; each set of said further group of sets having a different base unit in an additional, defined common position, the base units in the positions of the oligonucleotides which are not in a defined common position being randomized;

(e) assaying each of the sets of said further group of sets for specific activity for the target;

(f) selecting a set based upon its activity in said assay; and (g) performing steps (d), (e), and (f) iteratively to provide said cassette having each position defined.

32. A method for determining an oligonucleotide having specific assayable activity for a target comprising the steps of:

(a) preparing a group of sets of oligonucleotides, each oligonucleotide comprising at one predefined oligonucleotide cassette prepared by the method of claim 31 and at least one flanking region by:
  (i) defining it common position in a flanking region of the oligonucleotides of the sets, and
  (ii) synthesizing said sets of oligonucleotides such that each set has a different base unit in said common position, the base units which are not in said defined positions being randomized;

(b) assaying each of the sets for activity against the target;

(c) selecting a set based upon its activity in said assay;

(d) preparing a further group of sets of oligonucleotides, each of the sets of said further group of sets having in the previously defined common position the base unit appearing in the previously defined-common position in the previously selected set; each set of said further group of sets having a different base unit in an additional, defined common position, the base units in the positions of the oligonucleotides which are not in a defined position being randomized;

(e) assaying each of the sets of said further group of sets for specific activity for the target;

(f) selecting a set based upon its activity in said assay; and (g) performing steps (d), (e) and (f) iteratively until all positions of said oligonucleotide are identified, thereby determining an oligonucleotide having said specific, assayable activity.

33. A method for determining an oligonucleotide having specific, assayable activity for a non-antibody target comprising the steps of:

(a) preparing a group of sets of oligonucleotides, each oligonucleotide comprising at least four nucleotide units by:
  (i) defining a common position in the oligonucleotides of the sets, and
  (ii) synthesizing said sets of oligonucleotides such that each set has a different base unit in said common position, the base units which are not in said common position being randomized;

(b) assaying each of the sets for activity against the target;

(c) selecting a set based upon its activity against the target;

(d) preparing a further group of sets of oligonucleotides; each of the sets of said further group of sets having in the previously defined common position the base unit appearing in that position in the set selected in step (c); each set of said further group of sets having a different base unit in an additional, defined common position, the base units in the positions of the oligonucleotides which are not in a defined common position being randomized;

(e) assaying each of the sets of said further group of sets for specific activity for the target;

(f) selecting a set based upon its activity in said assay; and (g) performing steps (d), (e) and (f) iteratively until all positions of said oligonucleotide are identified, thereby determining an oligonucleotide having said specific, assayable activity.

34. The method of claim 33 wherein said group is comprised of from about three to about twenty sets.

35. The method of claim 33 wherein said group is comprised of four sets.

36. The method of claim 33 wherein said oligonucleotides are from 4 to about 20 nucleotide units in length.

37. The method of claim 33 wherein said group of sets of oligonucleotides is labeled with a delatable label.

38. The method of claim 37 wherein the group of sets of oligonucleotides is radiolabelled.

39. The method of claim 37 wherein said assay is streptavidin capture of biotinylated target, filter binding assay or affinity chromatography.

40. The method of claim 33 wherein the group of sets of oligonucleotides are sterically constrained.

41. The method of claim 33 wherein said target is a nucleic acid.

42. The method of claim 33 wherein said target is a carbohydrate.

43. The method of claim 33 wherein said target is a protein.

44. The method of claim 33 wherein said target is a glycoprotein.

45. The method of claim 33 wherein the target is a receptor, receptor binding ligand, antigen, enzyme, or transcription factor.

46. The method of claim 33 wherein the target is a phospholipase, tumor necrosis factor, endotoxin, interleukin, leukotriene, plasminogen activator, protein kinase, lipoxygenase, hydrolase, transacylase, or transcription factor.

47. The method of claim 33 wherein the target is a region of Epstein-Barr virus, rhinovirus, hepatitis virus, or influenza virus.

48. The method of claim 33 wherein the target is an RNA molecule or fragment thereof.

49. The method of claim 33 wherein the target is a region of a human immunodeficiency virus.

50. The method of claim 33 wherein the target is the TAR element of human immunodeficiency virus.

51. The method of claim 33 wherein the target is the gag-pol stem loop of human immunodeficiency virus.

52. The method of claim 33 wherein the target is the ras 47 base pair stem loop.

53. The method of claim 33 wherein the target is a region of a herpes virus.

54. The method of claim 33 wherein the target is a region of cytomegalovirus.

55. The method of claim 33 wherein the target is a region of an influenza virus.

56. The method of claim 33 wherein the target is endothelin-1.

57. The method of claim 33 wherein the target is leukotriene B-4.

58. The method of claim 33 wherein the target is human immunodeficiency virus gp 120.

59. The method of claim 33 wherein the target is the HIV tat protein.

60. The method of claim 33 wherein said assay is a gel shift assay.

61. The method of claim 33 wherein the target is a cell adhesion molecule.

62. The method of claim 33 wherein the target is a region of Candida, papillomavirus, human immunodeficiency virus, herpes simplex virus or cytomegalovirus.

63. A method for determining an oligonucleotide cassette having specific, assayable activity for a non-antibody target comprising the steps of:

(a) preparing a group of sets of oligonucleotides, each oligonucleotide comprising at least four base units by;
  (i) defining a common position in the oligonucleotides of the sets, and
  (ii) synthesizing said sets of oligonucleotides such that each set has a different base unit in said common position, the base units which are not in said common position being randomized;

(b) assaying each of the sets for activity against the target;

(c) selecting a set based upon its activity in said assay;

(d) preparing a further group of sets of oligonucleotides, each of the sets of said further group of sets having in the previously defined common position the base unit appearing in the previously defined common position in the previously selected set; each set of said further group of sets having a different base unit in an additional, defined common position, the base units in the positions of the oligonucleotides which are not in a defined common position being randomized;

(e) assaying each of the sets of said further group of sets for specific activity for the target; and (f) selecting a set based upon its activity in said assay; and (g) performing steps (d), (e), and (f) iteratively to provide said cassette having each position defined.

64. A method for determining an oligonucleotide having specific assayable activity for a non-antibody target comprising the steps of:

(a) preparing a group of sets of oligonucleotides, each oligonucleotide comprising at least one predefined oligonucleotide cassette prepared by the method of claim 63 and at least one flanking region by:
  (i) defining a common position in a flanking region of the oligonucleotides of the sets, and
  (ii) synthesizing said sets of oligonucleotides such that each set has a different base unit in said common position, the base units which are not in said defined positions being randomized;

(b) assaying each of the sets for activity against the target;

(c) selecting a set based upon its activity in said assay;

(d) preparing a further group of sets of oligonucleotides, each of the sets of said further group of sets having the previously defined common position the base unit appearing in the previously defined common position in the previously selected set; each set of said further group of sets having a different base unit in an additional, defined common position, the base units in the positions of the oligonucleotides which are not in a defined position being randomized;

(e) assaying each of the sets for specific activity for the target;

(f) selecting a set based upon its activity in said assay; and (g) performing steps (d), (e) and (f) iteratively until all positions of said oligonucleotide are identified, thereby determining an oligonucleotide having said specific, assayable activity.

* * * * *

UNITED STATES PATENT AND TRADEMARK OFFICE
CERTIFICATE OF CORRECTION

PATENT NO. : 5,672,472
DATED : September 30, 1997
INVENTOR(S) : Ecker et al.

It is certified that error appears in the above-indentified patent and that said Letters Patent is hereby corrected as shown below:

Column 1, line 26, please delete "Characteristic" and insert therefor --characteristic--;
Column 2, line 54, please delete "representing" and insert therefor --representation--;
Column 7, line 1, please delete "C$_3$" and insert therefor CF$_3$
Column 16, line 10, please delete "oligoeucleotide" and insert therefor --oligonucleotide--;
Column 20, Table 9, line 50, please delete "1.0" and insert therefor --10--;
Column 24, line 41, please delete "adenins" and insert therefor --adenine--;
Column 24, line 51, please delete "adenins" and insert therefor --adenine--;
Column 33, line 64, after the word "target" please insert the word --is--.

Signed and Sealed this

Twelfth Day of May, 1998

Attest:

*Attesting Officer*

BRUCE LEHMAN

*Commissioner of Patents and Trademarks*

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:1:

GGUGGUGGUG GGCGCCGUCG GUGUGGGCAA GAGUGCGCUG ACCAUCC      47

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: misc_feature
        ( B ) LOCATION: 4
        ( D ) OTHER INFORMATION: /note="pyrene analog of adenine"

( x i ) SEQUENCE DESCRIPTION: SEQ ID NO:2:

NNNANGNNNN      10

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: misc_feature
        ( B ) LOCATION: 4
        ( D ) OTHER INFORMATION: /note="pyrene analog of adenine"

( x i ) SEQUENCE DESCRIPTION: SEQ ID NO:3:

NNNANANNNN      10

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( i x ) FEATURE:
        ( A ) NAME/KEY: misc_feature
        ( B ) LOCATION: 4
        ( D ) OTHER INFORMATION: /note="pyrene analog of adenine"

( x i ) SEQUENCE DESCRIPTION: SEQ ID NO:4:

NNNANCNNNN      10

( 2 ) INFORMATION FOR SEQ ID NO:5:

( i ) SEQUENCE CHARACTERISTICS:
        ( A ) LENGTH: 10 base pairs
        ( B ) TYPE: nucleic acid (C) STRANDEDNESS: single
(D) TOPOLOGY: linear (ii) MOLECULE TYPE: RNA (genomic)

(ix) FEATURE:
   (A) NAME/KEY: misc_feature
   (B) LOCATION: 4
   (D) OTHER INFORMATION: /note="pyrene analog of adenine"

(xi) SEQUENCE DESCRIPTION: SEQ ID NO:5:

NNNANUNNNN    10

(2) INFORMATION FOR SEQ ID NO:6:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: RNA (genomic)

(xi) SEQUENCE DESCRIPTION: SEQ ID NO:6:

CCCUUCCANU C    11

(2) INFORMATION FOR SEQ ID NO:7:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: RNA (genomic)

(xi) SEQUENCE DESCRIPTION: SEQ ID NO:7:

CCCUUCCGNU C    11

(2) INFORMATION FOR SEQ ID NO:8:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: RNA (genomic)

(xi) SEQUENCE DESCRIPTION: SEQ ID NO:8:

CCCUUCCCNU C    11

(2) INFORMATION FOR SEQ ID NO:9:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: RNA (genomic)

(xi) SEQUENCE DESCRIPTION: SEQ ID NO:9:

CCCUUCCUNU C    11

(2) INFORMATION FOR SEQ ID NO:10:

(i) SEQUENCE CHARACTERISTICS:
      (A) LENGTH: 11 base pairs
      (B) TYPE: nucleic acid ( C ) STRANDEDNESS: single
( D ) TOPOLOGY: linear ( i i ) MOLECULE TYPE: RNA (genomic)

( x i ) SEQUENCE DESCRIPTION: SEQ ID NO:10:

CCCUUCCCAU C    11

( 2 ) INFORMATION FOR SEQ ID NO:11:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:11:

CCCUUCCCGU C    11

( 2 ) INFORMATION FOR SEQ ID NO:12:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:12:

CCCUUCCCCU C    11

( 2 ) INFORMATION FOR SEQ ID NO:13:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:13:

CCCUUCCCUU C    11

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:14:

GCGNNNANNN NNCGC    15

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:15:

GCGNNNGNNN NNCGC                15

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:16:

GCGNNNCNNN NNCGC                15

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:17:

GCGNNNUNNN NNCGC                15

( 2 ) INFORMATION FOR SEQ ID NO:18:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AAGACGTCTT GCG                  13

( 2 ) INFORMATION FOR SEQ ID NO:19:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TCTGCAGAAC GC                   12

( 2 ) INFORMATION FOR SEQ ID NO:20:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:20:

GCCAGAUCUG AGCCUGGGAG CUCUCUGGC     29

( 2 ) INFORMATION FOR SEQ ID NO:21:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:21:

CUGGCCUUCC UACAAGGGAA GGCCAG    2 6